(12) United States Patent
Hattori

(10) Patent No.: US 8,222,400 B2
(45) Date of Patent: Jul. 17, 2012

(54) CYCLODEXTRIN COMPOUND MODIFIED WITH FOLIC ACID, PROCESS FOR PRODUCTION THEREOF, DRUG DELIVERY AGENT FOR TARGETING DRUG DELIVERY SYSTEM, PHARMACEUTICAL COMPOSITION, AND IMAGING AGENT

(75) Inventor: Kenjiro Hattori, Kanagawa (JP)

(73) Assignee: Nanodex Inc., Kanagawa (JP)

( * ) Notice: Subject to any disclaimer, the term of this patent is extended or adjusted under 35 U.S.C. 154(b) by 242 days.

(21) Appl. No.: 12/679,516

(22) PCT Filed: Sep. 26, 2008

(86) PCT No.: PCT/JP2008/067566
§ 371 (c)(1),
(2), (4) Date: Mar. 23, 2010

(87) PCT Pub. No.: WO2009/041666
PCT Pub. Date: Apr. 2, 2009

(65) Prior Publication Data
US 2010/0209347 A1    Aug. 19, 2010

(30) Foreign Application Priority Data

Sep. 28, 2007   (JP) ................................. 2007-256527

(51) Int. Cl.
*C08B 37/16*   (2006.01)
*A01N 43/04*   (2006.01)
*A61K 31/715*  (2006.01)

(52) U.S. Cl. ......................................... 536/103; 514/58
(58) Field of Classification Search ........................ None
See application file for complete search history.

(56) References Cited

U.S. PATENT DOCUMENTS

| 2004/0077595 A1 | 4/2004 | Cheng et al. |
| 2008/0058427 A1 | 3/2008 | Cheng et al. |

OTHER PUBLICATIONS

Hattori et al. Journal of Inclusion Phenomena and Macrocyclic Chemistry (2006) 56:9-16.*
Salmaso et al. Bioconjugate Chem. 2004, 15, 997-1004.*
International Search Report for PCT/JP2008/067566; Jan. 6,2009.
S. Wang, et al., Folate-mediated targeting of antineoplastic drugs, imaging agents, and nucleic acids to cancer cells, Journal of Controlled Release, Apr. 30, 1998, p. 39-48, vol. 53, Issues 1-3, Elsevier Science B.V., Amsterdam.
Philip S. Low,et al., Discovery and Development of Folic-Acid-Based Receptor Targeting for Imaging and Therapy of Cancer and Inflammatory Diseases., Accounts of chemical research., Jan. 2008, p. 120-129, vol. 41 Issue 1, American Chemical Society, Washington.
Y. C. Lee, et al., Carbohydrate-Protein Interactions: Basis of Glycobiology., proteomics, Accounts of chemical research, 1995, pp. 321-327, vol. 28 Issues 8, American Chemical Society, Washington.
P. Caliceti, et al., Synthesis and Physicochemical Characterization of Folate-Cyclodextrin Bioconjugate for Active Drug Delivery., Bioconjugate Chemistry., 2003, pp. 899-908, vol. 14 Issues 5, American Chemical Society, Washington.
S. Salmosa, et al. Specific Antitumor Targetable β-Cyclodextrin-Poly(ethylene Glycol)-Folic Acid Drug Delivery Bioconjugate., Bioconjugate Chemistry, Aug. 2004, p. 997-1004, vol. 15 Issues 5, American Chemical Society, Washington.
S. Salmosa, et al., New cyclodextrin bioconjugates for active tumour targeting, Journal of Drug Targeting, Jul. 2007, p. 379-390, vol. 15, No. 6, Informa Healthcare, London.
K. Hattori, et al., Saccharide-branched Cyclodextrins as Targeting Drug Carriers, Journal of Inclusion Phenomena and Macrocyclic Chemistry, Oct. 2006, p. 9-16, vol. 56, No. 1-2, Springer, Secaucus, NJ.
Extended European Search Report mailed Dec. 5, 2011, issued in corresponding Application No. EP 08833790 (4 pages).
F. Hirayama, et al., Cyclodextrin-based controlled drug release system, Advanced Drug Delivery Reviews, 1999, p. 125-141, vol. 36, Issue 1, Elsevier B.V., Amsterdam.

* cited by examiner

*Primary Examiner* — Layla Bland
(74) *Attorney, Agent, or Firm* — Pearne & Gordon LLP

(57) ABSTRACT

Disclosed is a cyclodextrin compound comprising glucopyranoses constituting cyclodextrin, the glucopyranoses having substituents each having folic acid substituted for two or more primary hydroxy groups at position-6 of the glucopyranoses.

7 Claims, 3 Drawing Sheets

CYCLODEXTRIN COMPOUND MODIFIED WITH FOLIC ACID, PROCESS FOR PRODUCTION THEREOF, DRUG DELIVERY AGENT FOR TARGETING DRUG DELIVERY SYSTEM, PHARMACEUTICAL COMPOSITION, AND IMAGING AGENT

THE FIELD OF THE INVENTION

The present invention relates to cyclodextrin compounds modified with folic acid, processes for production thereof, and drug delivery agents, in particular, to a cyclodextrin compound which is used as a drug delivery agent used for a targeting drug delivery system (TDDS) (hereafter, simply sometimes referred to as "CD compound"), and a process for production thereof. The TDDS is developed for a target that overexpresses a folate receptor particularly in cancer cells, etc. The present invention, in particular, relates to a cyclodextrin compound comprising glucopyranoses constituting cyclodextrin, the glucopyranoses having substituents each having folic acid substituted for two or more primary hydroxy groups at position-6 of the glucopyranoses, and a process for production thereof. A target protein is recognized by the folic acid. The invention also relates to a drug delivery agent, a pharmaceutical composition, and an imaging agent all of which contain the cyclodextrin compound and are used in a targeting system. The targeting system has superior characteristics ("stealth agent", the recognition of cancer cells, superior drug delivery).

DESCRIPTION OF THE RELATED ART

Cancer cell targeting drug delivery system (hereinafter, simply referred to as "cancer cell TDDS") comprises a ligand (recognition tag) for a receptor (target site) possessed by a target, a carrier (e.g., liposome, cyclodextrin), and a drug (doxorubicin, paclitaxel, curcumin, etc.).

The studies have been conducted to show that folic acid, as the above tag for cancer cells, is introduced into liposomes, polymer micelles, and the like as a subject of practical research applications.

Two reviews (see, S. Wang, Philip S. Low, J. Control. Release, 53, 39-48 (1998); Philip S. Low, Walter A. Henne, Derek D. Doorneweerd, Accounts Chem. Research 41, 120-129 (2008)) disclose that folic acid, a type of vitamins, binds strongly to a folate receptor protein which is overexpressed on the surface of cancer cells (hereinafter, simply referred to as "FBP") at the association constant of $10^{10} M^{-1}$. A report (see, Philip S. Low, Walter A. Henne, Derek D. Doorneweerd, Accounts Chem. Research 41, 120-129 (2008)) has indicated that folic acid is effective in the recognition of the sites of inflammation. The types of cancer (as a subject in this report) include ovarian cancer, endometrial cancer, kidney cancer, lung cancer, breast cancer, brain cancer, testicular cancer, ovarian cancer, bone marrow cancer and the like. The delivered drugs include, in addition to anticancer drugs, protein toxins, imaging agents, antisense oligonucleotides, genes and the like.

A study (see, Y. C. Lee and R. T. Lee, Acc. Chem. Res, 1995, 28) has shown that the addition of a plurality of recognition tags to CD, if appropriately shown in certain spatial arrangements, can simultaneously induce one or more interactions of the ligands with a plurality of binding sites of a cell surface receptor protein. Each interaction contains a weak bond composed of a hydrogen bond. As the number of interactions increases, the interactions progressively (exponentially) become stronger. The interaction is a regioselective and strong interaction, characterized by having an association constant equal to the association constant (approximately $10^{10} M^{-1}$) of the antigen-antibody reaction. The study has described this effect as what is called the "Glyco-cluster effect".

The group of Caliceti et al. from Padova University, Italy, has reported a cyclodextrin compound modified with folic acid. Realistically, there is no practical targeting drug delivery system (TDDS) using folic acid for cancer cells (see, P. Caliceti, S. Salmaso, A, Semenzato, T. Carofiglio, R. Formasier, M. Fermeglia, M. Ferrone, S. Pricl, Bioconjuate Chem., 14, 899-908 (2003); S. Salmaso, A. Semenzato, P. Caliceti, J. Hoebeke, F. Sonvico, C. Dubernet, P. Couvreur, Bioconjugate Chem., 15, 997-1004 (2004); S. Salmaso, S. Sara, A. Semenzato, P. Caliceti, J. Drug Targeting, 15(6), 379-390 (2007)).

In particular, they introduced a 700 Da (tetradecamer) diamino-polyethylene glycol compound (hereinafter, simply referred to "diamino-PEG compound") into monotosyl-activated β-cyclodextrin, and then obtained a cyclodextrin compound modified with folic acid (hereinafter, simply referred to as "CD-PEG-FA") by the reaction with succinimidyl ester-activated folic acid (see, P. Caliceti, S. Salmaso, A, Semenzato, T. Carofiglio, R. Fornasier, M. Fermeglia, M. Ferrone, S. Pricl, Bioconjugate Chem., 14, 899-908 (2003)). The interaction between the CD-PEG-FA and immobilized FBP has been evaluated by the surface plasmon resonance (SPR) analysis. The uptake thereof into human oral cancer cells (KB) after 2 hours has also been analyzed by a confocal laser scanning microscope. Furthermore, as a new process for production, five hexamethylenediisocyanate were introduced into β-CD, and the above diamino-PEG compounds were conjugated therewith. Then, a compound in which folic acid was introduced into one of those PEG compounds was obtained (hereinafter, the compound is simply referred to as "CD-(C6-PEG)5-FA"). The biodegradable characteristics, improvements of the solubility of drugs such as β-estradiol, curcumin, etc., and the like were evaluated. Furthermore, the targeting of the above compound containing supported curcumin to human oral cancer cells (KB) or human lung cancer cells (MCF) was evaluated (see, S. Salmaso, S. Sara, A. Semenzato, P. Caliceti, J. Drug Targeting, 15(6), 379-390 (2007)).

While these cyclodextrin modified with one substituent having folic acid (CD-PEG-FA and CD-(C6-PEG)5-FA) recognize KB cancer cells, the degree of uptake is qualitative and not clear. The ability to deliver anticancer drugs is also not clear. The process for production is also not clear. The association constant of the foregoing compound was low, and was approximately $10^3 M^{-1}$. The practicality of the compound is low.

A primary hydroxy group is present at position-6 in a glucopyranose that constitutes cyclodextrin (CD). When the number of the glucopyranose that constitutes CD is six, for example, six primary hydroxy groups are present in CD. The inventor and others have reported the synthesis of a CD compound in which the primary hydroxy groups (a plurality of the groups are present in CD) are independently substituted by a galactose spacer arm which is produced by conjugating a sugar chain (see, K. Hattori, A. Kenmoku, T. Mizuguchi, D. Ikeda, M. Mizuno, T. Inazu, J. Inclusion Phenom. Macrocyclic Chem., 56, 9-16 (2006)). They have also reported that the compound has what is called "dual recognition" capabilities (i.e. very high assembly capabilities to bind both a drug and lectin).

SUMMARY OF THE INVENTION

It is an object of the present invention to provide cyclodextrin compounds that are superior in association with a target or superior in drug-inclusion capabilities (capabilities to form inclusion complexes containing drugs), and processes for production thereof. An aspect of the invention also provides targeting drug delivery agents, pharmaceutical compositions, and targeting imaging agents all of which contain the cyclodextrin compounds. In particular, it is an object of the present invention to provide a cyclodextrin compound that has two or more simultaneous interactions of two or more folic acids with the binding sites for folic acid. The compound has a superior association with cancer cells, and even superior drug-inclusion capabilities. An aspect of the invention also provide a process for production thereof, and a targeting drug delivery agent, a pharmaceutical composition, and a targeting imaging agent all of which contain the cyclodextrin compound.

According to the invention, the following means are provided:

(1) A cyclodextrin compound comprising glucopyranoses constituting cyclodextrin, the glucopyranoses having substituents each having folic acid substituted for two or more primary hydroxy groups at position-6 of the glucopyranoses.

(2) The cyclodextrin compound of the (1), wherein the compound is represented by the general formula 1:

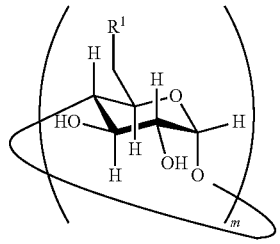

General formula 1

In the general formula 1, m represents an integer of 6 to 8;

each $R^1$ is independently selected from a substituent having folic acid, a hydroxy group, a substituent having a glycosyl group, a hydrophilic group; the number of the substituent having folic acid is at least two in the cyclodextrin compound; a hydroxyl group other than the hydroxyl group of the compound may be substituted by a substituent having a glycosyl group or a hydrophilic group; and the substituent having folic acid is represented by the general formula 2:

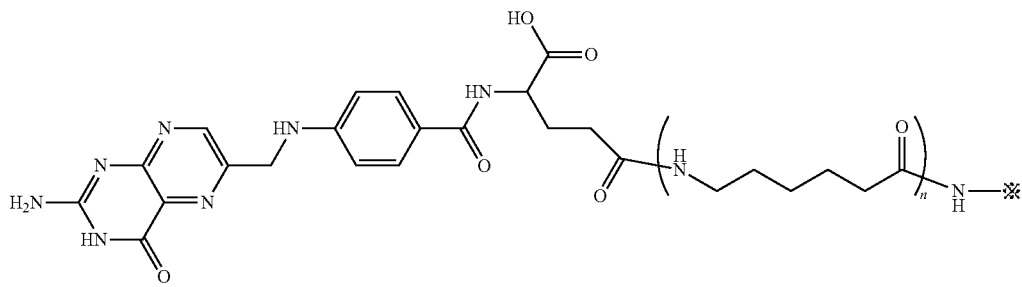

General formula 2

In the general formula 2, the "※" represents a binding position with a carbon atom at position-6 in a glucopyranose constituting cyclodextrin;

n represents an integer of 0 to 3; and when n=0, a portion between a carbonyl carbon atom and an amino nitrogen atom represents a single bond;

(3) The cyclodextrin compound of the (2), wherein the compound is represented by any one of the formulae:

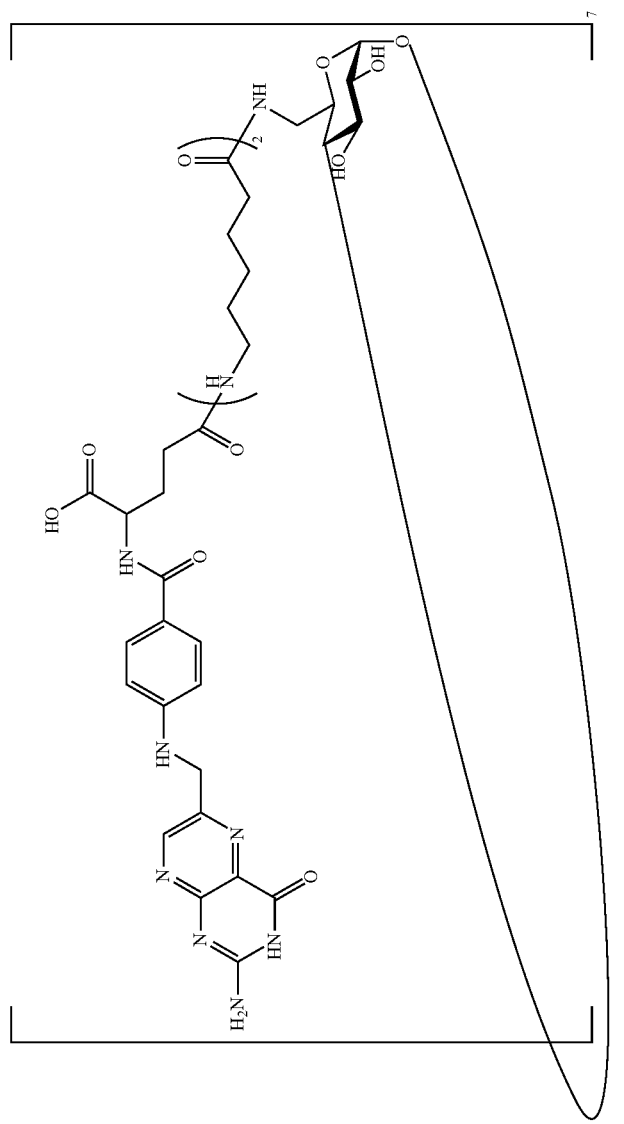
Exemplary compound 1

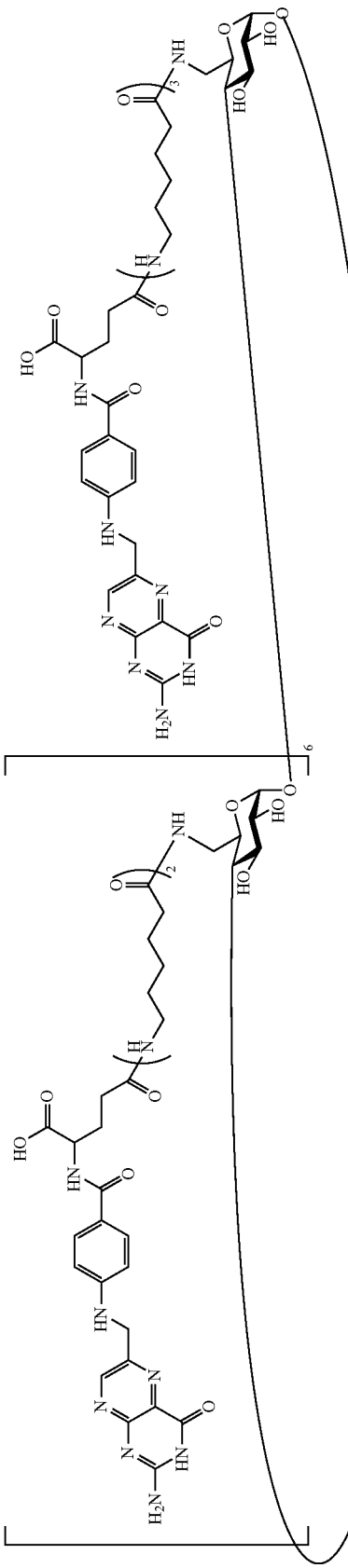
Exemplary compound 7
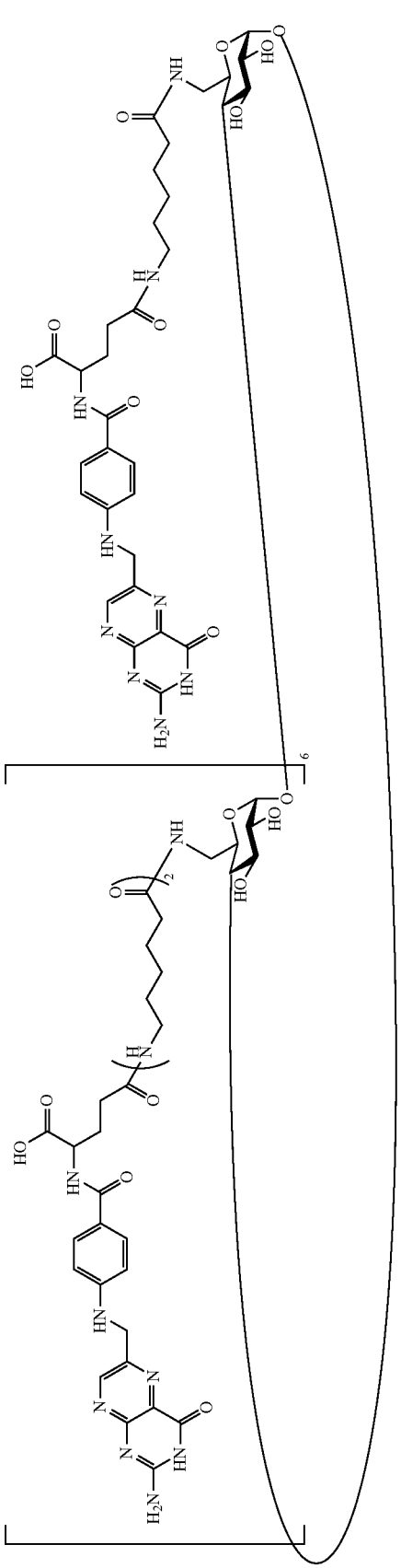
Exemplary compound 8

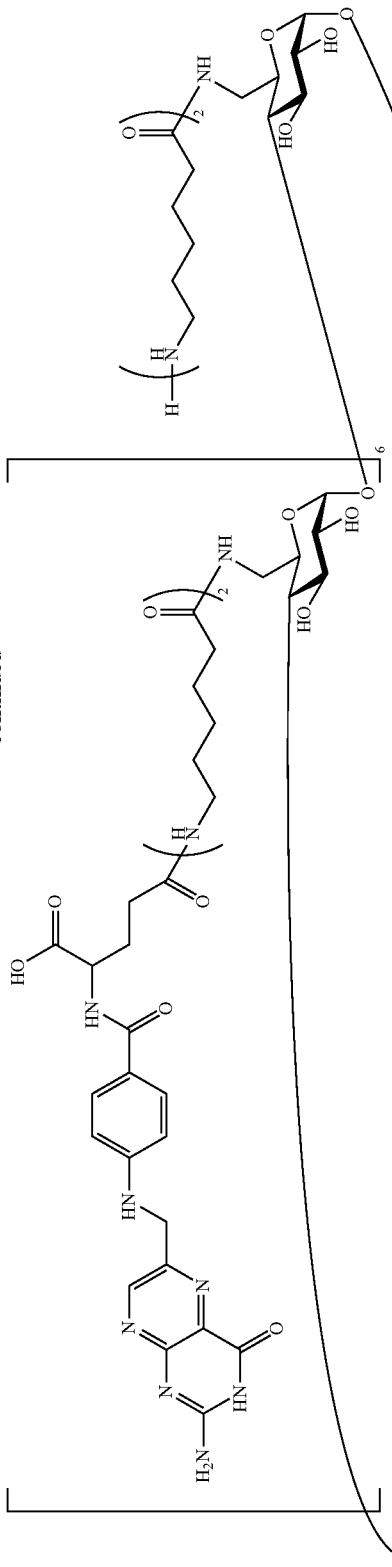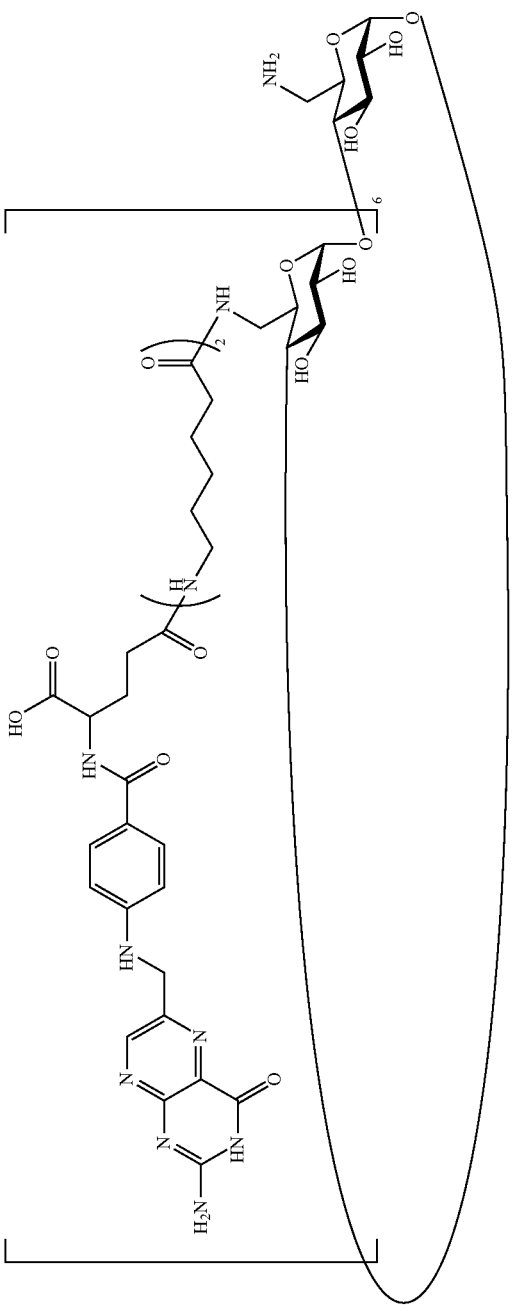

(4) A process for producing a cyclodextrin compound modified with folic acid, comprising the step of condensing folic acid with a cyclodextrin, the cyclodextrin having an amino group or an amino-oligocaproamide group substituted for a primary hydroxy group at position-6 in each glucopyranose constituting a cyclodextrin ring.

(5) A targeting drug delivery agent containing the cyclodextrin compound of any one of the (1)-(3).

(6) A targeting pharmaceutical composition containing a drug and the cyclodextrin compound of any one of the (1)-(3), wherein the drug is included in the cyclodextrin compound.

(7) A targeting imaging agent containing an imaging agent and the cyclodextrin compound of any one of the (1)-(3), wherein the imaging agent is included in the cyclodextrin compound.

The foregoing and other features and advantages of the present invention will become more apparent from the following descriptions and the attached drawings.

BEST MODE FOR CARRYING OUT THE INVENTION

Figure 1:
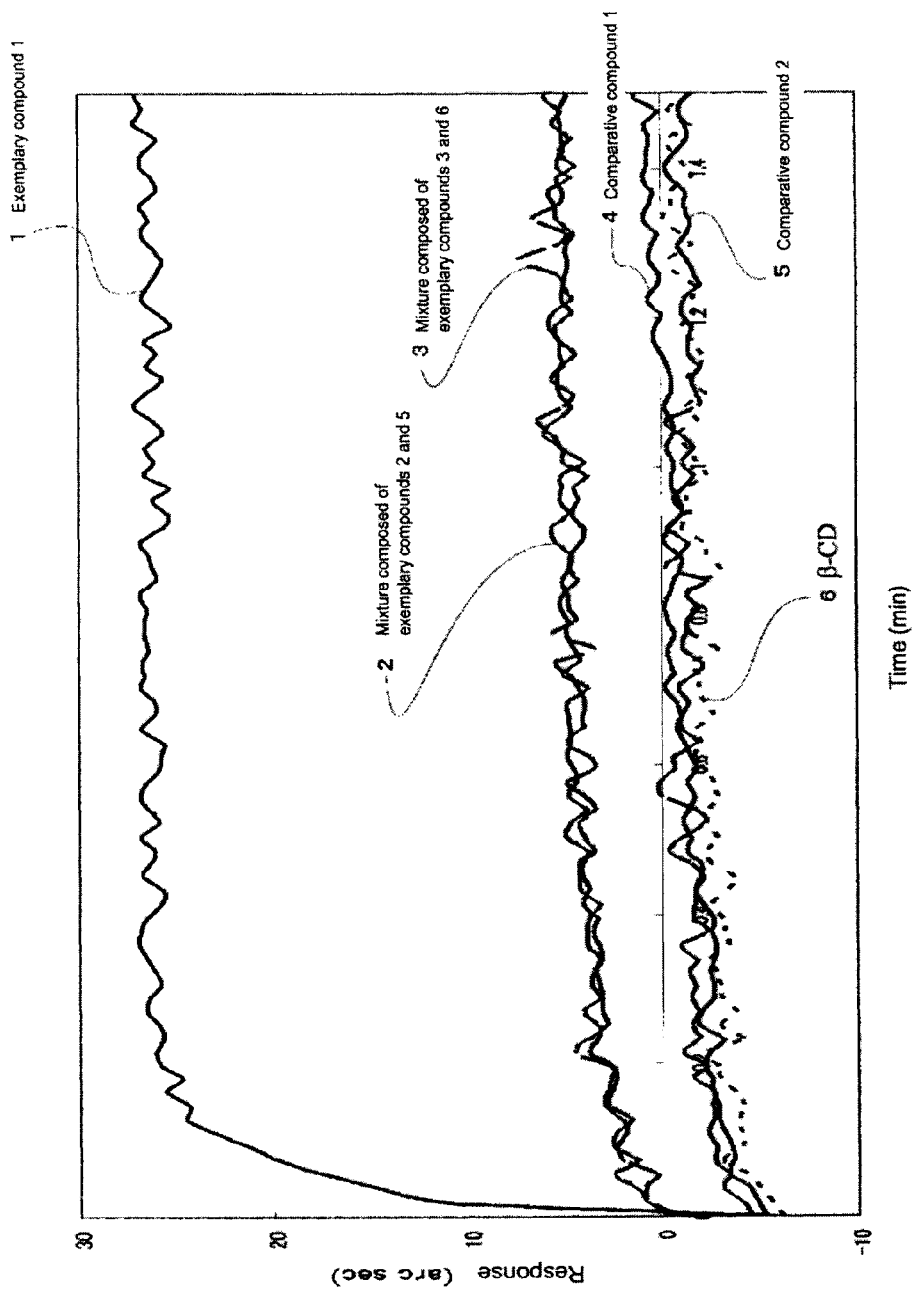
FIG. 1 is a diagram showing the results of the SPR measurements, indicating the interaction of FBP with the exemplary compound 1, etc., as comparative examples, the comparative compound 1 or 2, or unmodified β-CD.

First, a cyclodextrin compound of the present invention is described.

A cyclodextrin compound of the invention is a cyclodextrin compound comprising glucopyranoses constituting cyclodextrin, the glucopyranoses having substituents each having folic acid substituted for two or more primary hydroxy groups at position-6 of the glucopyranoses.

The cyclodextrin compound of the invention is preferably represented by the following general formula I:

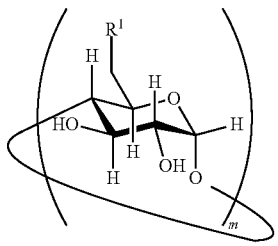

General formula 1

In the general formula 1,
m represents an integer of 6 to 8;
each $R^1$ is independently selected from a substituent having folic acid, a hydroxy group, a substituent having a glycosyl group, a hydrophilic group; and the substituent having folic acid is represented by the following general formula 2:
the number of the substituent having folic acid is at least two in the cyclodextrin compound.

When m=6, α-cyclodextrin ring is constituted;
when m=7, β-cyclodextrin ring is constituted;
when m=8, γ-cyclodextrin is constituted.

The larger m is, the larger the diameter of the cavity of the cyclodextrin ring becomes. The cyclodextrin ring cannot contain giant molecules and proteins, and a substance to be contained within the cavity is preferably a hydrophobic and insoluble guest drug. In addition, since the cyclodextrin compounds (1-5 nm) are smaller than liposomes and polymer micelles (100 nm), better penetration from the cell surface and easy movement within tissues or the blood-brain barrier are achieved.

As described below, the m is determined by considering the molecular size of a drug to be contained within the cyclodextrin compound, and preferably represents an integer of 7. In the cyclodextrin compound, the number of the substituent having the folic acid is two or more, preferably m minus 1, or particularly m.

A hydroxyl group other than the substituted hydroxyl group of the cyclodextrin compound may be substituted by one of substituents each having a glycosyl group or a hydrophilic group.

The substituents having a hydrophilic group include, from the viewpoint of adding hydrophilic properties to the cyclodextrin compounds of the invention, a hydroxymethylcarbonyl group (—OCOCH$_2$OH) that is obtained by the esterification reaction with hydroxyacetic acid, a gluconate group that is obtained by the esterification reaction with gluconic acid, and the like.

The general formula 2:

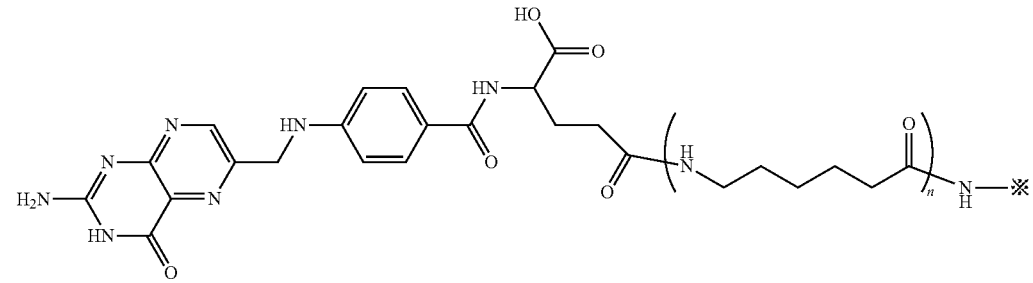

General formula 2

In the general formula 2,
the "✕" represents a binding position with a carbon atom at position-6 in a glucopyranose constituting cyclodextrin;
n represents an integer of 0 to 3; and
when n=0, a portion between a carbonyl carbon atom and an amino nitrogen atom represents a single bond. As described below, n preferably represents an integer of 1 or 2, particularly prefers to represent an integer of 2.

In the general formula 2, the portion represented by the following formula is repeated units derived from aminocaproic acid as a spacer arm described below.

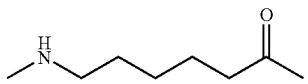

Thus, hereinafter, the portion represented by the above formula may be herein simply represented by the "cap". Accordingly, the general formula 2 can also be represented by the following formula.

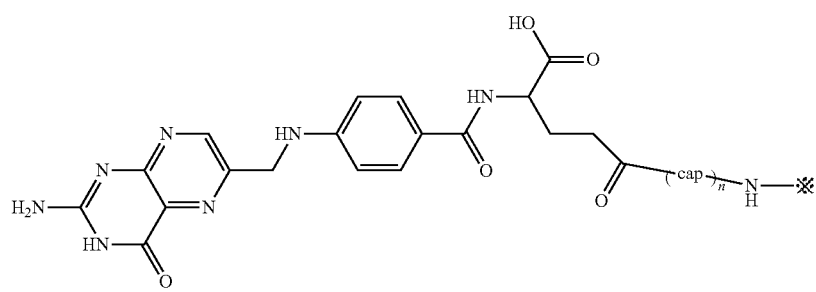

General formula 2

The "✕" and n in the general formula 2 are described previously.
When n=2 herein, the portion may simply refer to cap2. When n=1, the portion may sometimes simply refer to cap1.
In addition, when n=0, the cap represents a single bond between the carbonyl carbon atom and the amino nitrogen atom in the formula.

The repeated units derived from aminocaproic acid as this spacer arm are preferred from the viewpoint of the following 1) and 2).

1) To achieve what we call the "Nano-cluster effect" (simultaneous associations between a plurality of folic acids and a plurality of folate receptors (e.g., cancer cell surface)), the appropriate length can be provided.

2) The pentamethylene moiety is hydrophobic, and the drug-inclusion capabilities are enhanced by the "Sea anemone effect".

It has been reported that the higher-order structure of the folate receptor has two folate binding sites among the subunits of the tetramer, which was revealed through crystal structure analysis of glycine-N-methyltransferase, an enzyme for which inhibitor is folic acid (for example, see Z. Luka, S. Pakhomova, L. V. Loukachevitch, M. Egli, M. E. Newcomer, C. Wagner, J. Biol. Chem., 282, 4069-4075 (2007)). Accordingly, from the biological homology, the folate receptors in cancer cells are presumed to have a similar structure having the Glyco-cluster effect., and a plurality of folic acids is considered to exert multiple and simultaneous interactions with its binding sites. Such an effect may refer to the "Nano-cluster effect", using the analogy from the Glyco-cluster effect (i.e., an effect resulting from the spatial arrangement and receptor topology of sugar chans).

Because the cyclodextrin, in which a plurality of the spacer arms are modified, has enough abilities to form the inclusion complexes containing drugs by the Sea anemone effect (see K. Hattori, A. Kenmoku, T. Mizuguchi, D. Ikeda, M. Mizuno, T. Inazu, J. Inclusion Phenom. Macrocyclic Chem., 56, 9-16 (2006)) and has the intended association constant over $10^6 M^{-1}$, the drugs can also be delivered efficiently.

In the cyclodextrin compound represented by the general formula 1, $R^1$ may be a substituent having folic acid, the substituent represented by the following general formula 3. The number of the substituent having folic acid is at least two in the cyclodextrin compound as described above.

The general formula 3:

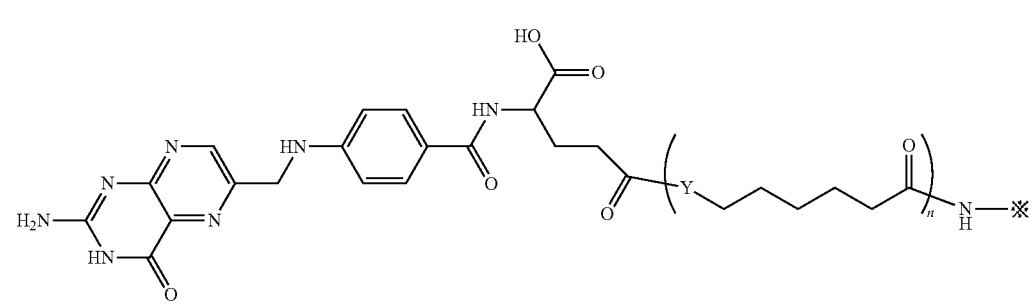

General formula 3

In the general formula 3, Y represents an oxygen atom or a sulfur atom. The "✕" and n are as described above.

Instead of using aminocaproic acid which is repeated units as a spacer arm, the substituent can be produced by using 6-hydroxycaproic acid when Y is an oxygen atom, or by using mercaptocaproic acid when Y is a sulfur atom.

The cyclodextrin compound represented by the general formula 1 may be herein simply represented by the following general formula a:

General formula a

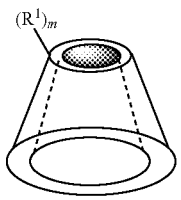

$(R^1)_m$

In the general formula a, $R^1$ and m are described above;

each $R^1$ independently represents a substituent having folic acid, a hydroxy group, a substituent having a glycosyl group, or a hydrophilic group; the substituent having the folic acid is represented by the general formula 2; and the number of the substituent having folic acid is at least two in the cyclodextrin compound. The cyclodextrin compound (CD) of the invention is preferably the compound represented by the following general formula b:

General formula b

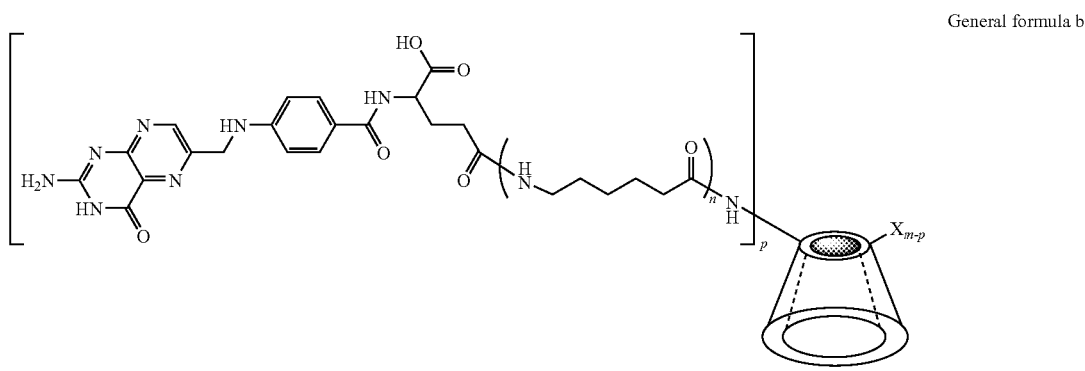

In the general formula b, m and n are as described above;

p is an integer of two or more and m or less;

(m minus p) X each independently represents a hydroxy group, a substituent having a glycosyl group, or a hydrophilic group. The substituent having the glycosyl group adds hydrophilicity to the cyclodextrin (CD) compound of the invention.

The glycosyl group in the substituent is preferably those recognized specifically by the target proteins of the specific target diseases (liver cancer, colon cancer, inflammation, etc.). In the viewpoint of ease of availability and synthesis, preferred is an oligosaccharide (a carbohydrate having 1-4 sugar residues long) or a sugar chain. Considering the target diseases (liver cancer, colon cancer, inflammation, etc.) of the targeting drug delivery system (TDDS), more preferred is a monosaccharide (i.e., a galactosyl group, a fucosyl group, a glucosyl group, a mannosyl group).

The substituents having the glycosyl group include a 1-glycosyl-oxypropylthioethyl amide group, a 1-glycosyl-oxypropylthioethylamidehexanoylamide group having the above cap as a spacer arm (sometimes referred to as a "1-glycosyl-oxypropylthioethylamide-cap1 group"), a 1-glycosyl-oxypropylthioethylamidehexanoylamidehexanoylamide group (sometimes referred to as a "1-glycosyl-oxypropylthioethylamide-cap2 group"), and the like. The glycosyl groups in the substituents are preferably α-D-galactosyl, α-L-fucosyl, α-D-mannosyl or α-D-glucosyl.

The following exemplary compounds 1-10 are represented as specific examples of the cyclodextrin compound of the invention. The present invention, however, is not limited to these.

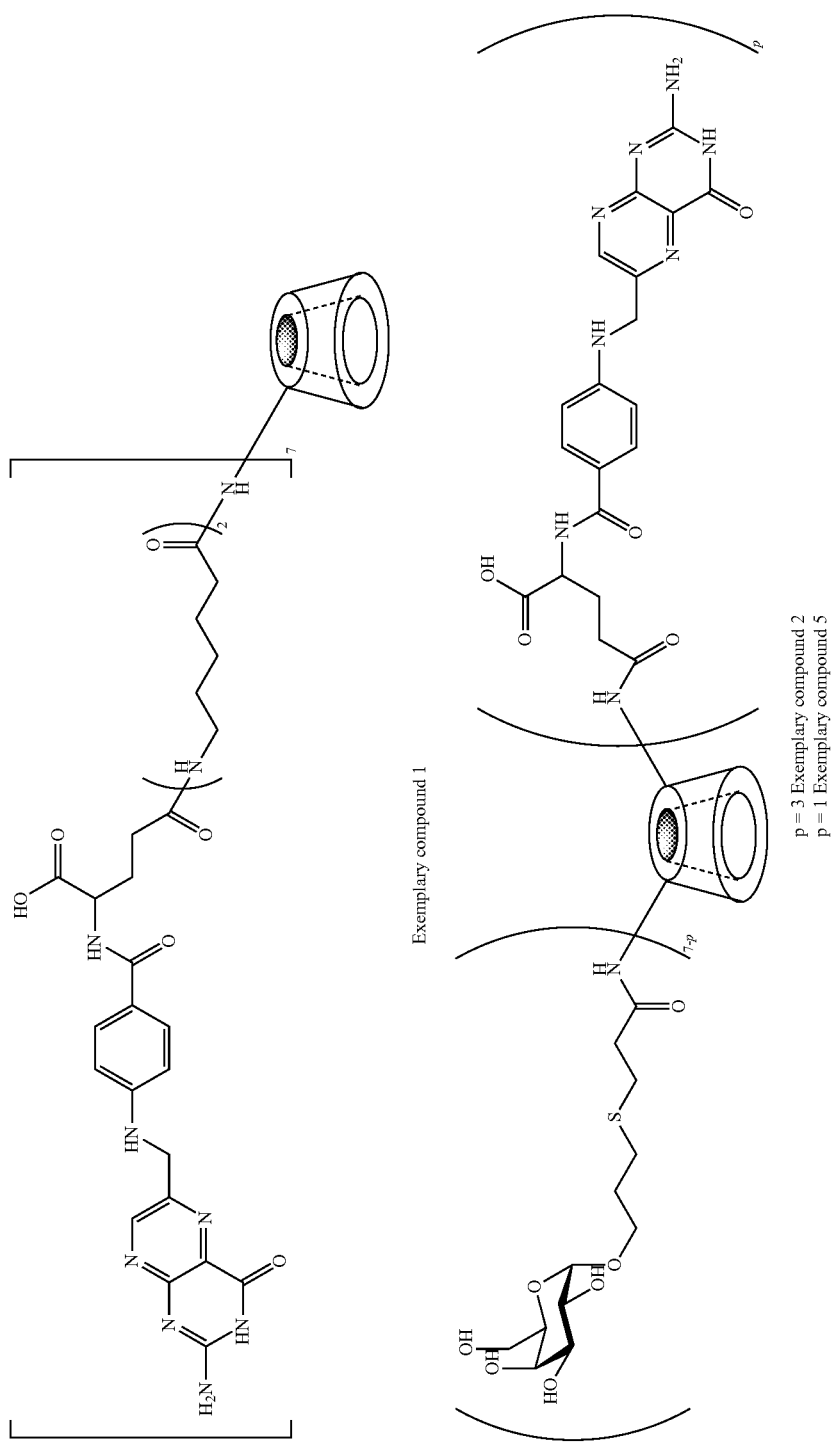

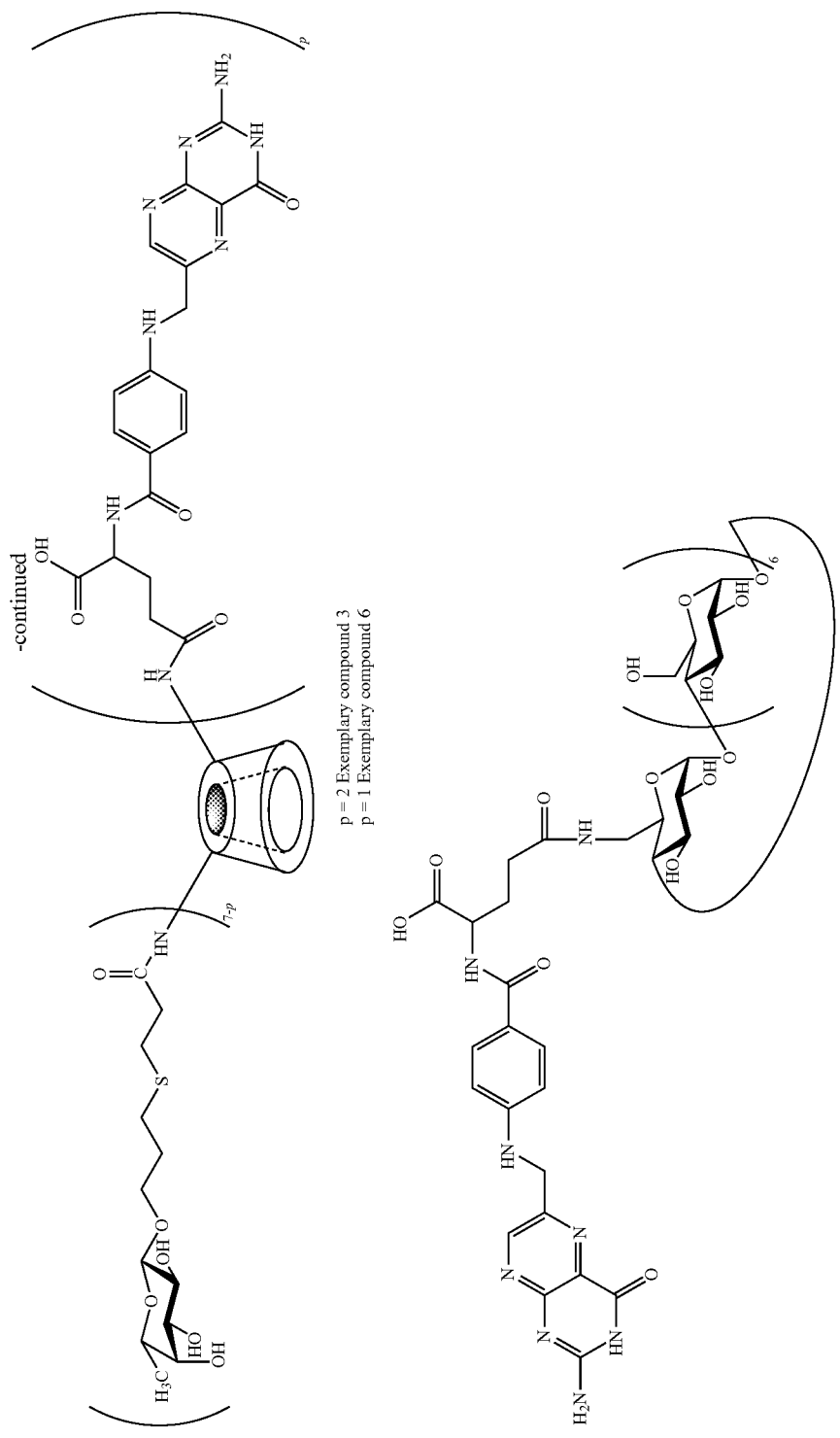

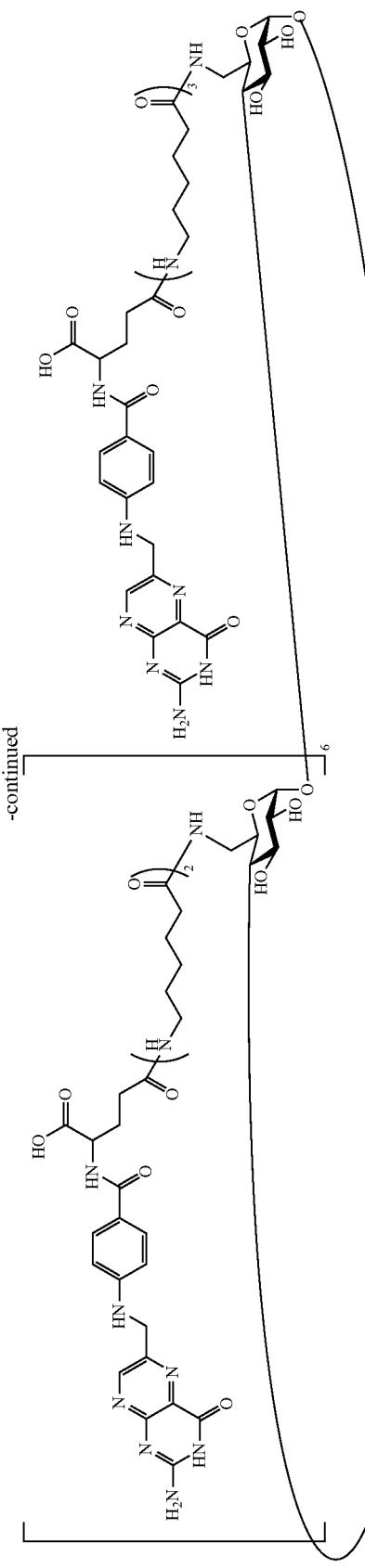
Exemplary compound 7
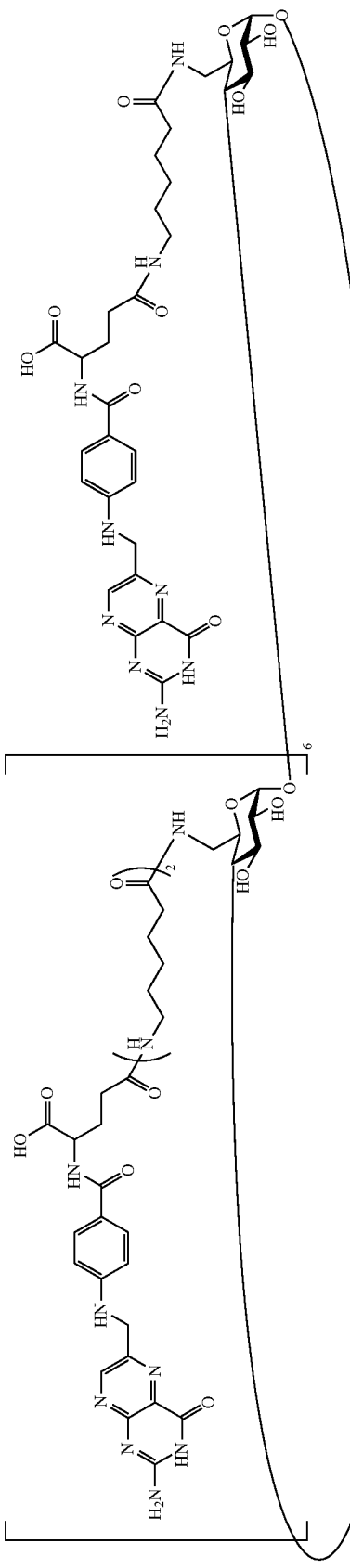
Exemplary compound 8

-continued
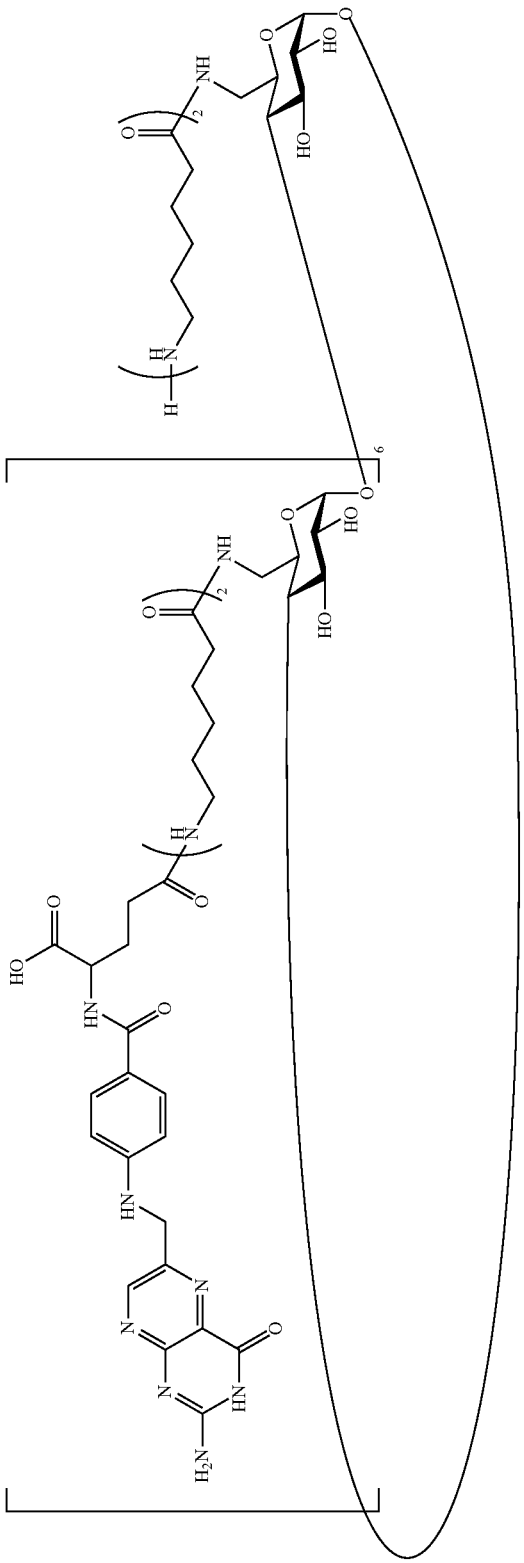
Exemplary compound 9
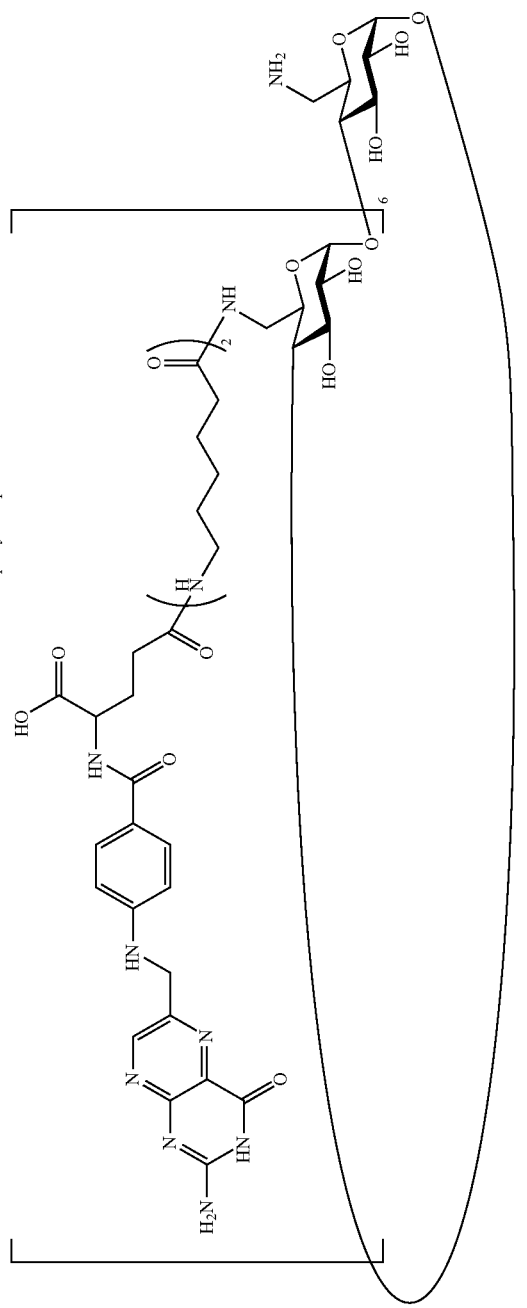
Exemplary compound 10

The cyclodextrin (CD) that is used as a starting material for the invention is then described.

The CDs that are used as a starting material for the invention are not particularly limited as long as having a basic skeleton of cyclodextrin, and include α-CD, β-CD, and γ-CD. These CDs differ in the number of glucopyranoses that constitutes a ring (α: 6 portions; β: 7 portions; γ: 8 portions), and also differ in the diameter of the cavity according to the number (α: 0.45 nm; β: 0.70 nm; γ: 0.85 nm). For example, α-CD is large enough to incorporate a benzene ring, and can form the inclusion complexes containing trichloroethylene, tetrachloroethylene, and the like. In addition, β-CD is large enough to incorporate a naphthalene ring. γ-CD is large enough to incorporate two anthracene or naphthalene rings. Accordingly, those skilled in the art can appropriately select the CD having the optimal diameter of the cavity in consideration of the molecular size of drugs that should be incorporated in the inclusion complexes.

Next, a process for producing the cyclodextrin compounds of the invention is described.

The process for producing the CD compounds of the invention comprising the step of condensing folic acid with a cyclodextrin, the cyclodextrin having an amino group or an amino-oligocaproamide group substituted for a primary hydroxy group at position-6 in each glucopyranose constituting a cyclodextrin ring. The process for producing the CD compound of the invention is preferably characterized by the reaction of folic acid with the CD having functional groups or the CD having a spacer arm (i.e., a structure in order to have a proper distance between a CD ring and folic acid) at all the primary hydroxy groups at position-6 in each glucopyranose constituting a cyclodextrin ring, under the presence or absence of a condensation agent.

The cyclodextrins (CD), which are used in the process for production, having the functional groups are described.

In the present invention, CD having functional groups is preferably produced by substituting all the primary hydroxy groups at position-6 in each glucopyranose constituting a CD ring by functional groups. Introduction of the functional groups to CD can be carried out by any methods that are used by those skilled in the art.

The functional groups of the CD having functional groups at primary hydroxy groups at position-6 in each glucopyranose that constitutes a CD ring, include an amino group, ether group, thioether group, carboxyl group, azido group, p-toluenesulfonyl group, epoxide group, unsaturated group, thiol group, acetoxy group, phenoxy group, and halogen groups (such as iodine, bromine, chlorine), etc. The amino group is more preferred because the amino group has certain reactivity to folic acid.

As a specific example, heptakis-6-amino-β-cyclodextrin substituting all the primary hydroxy groups at position-6 in each glucopyranose molecule that constitutes a cyclodextrin (CD) ring by amino groups (the following formula 1) (hereafter, sometimes simply referred to as "peraminated CD") can be obtained by peramination after chlorination (what is called perchlorination) and perazidation of all the hydroxy groups at position-6 in each glucopyranose molecule.

Next, the foregoing CD having the spacer arms at primary hydroxy groups at position-6 in each glucopyranose molecule that constitutes a cyclodextrin (CD) ring is described.

The CD having the spacer arms can be constructed by the condensation reaction of the CD having functional groups at primary hydroxy groups at position-6 in each glucopyranose molecule that constitute a CD ring, with one or more aminocaproic acids as a spacer arm. The condensation reaction is represented by the following scheme.

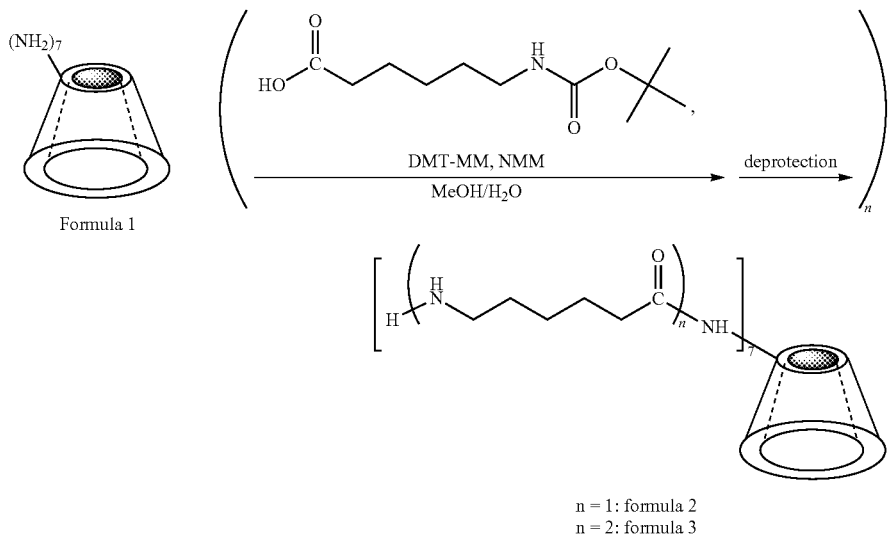

n = 1: formula 2
n = 2: formula 3

Specifically, the condensation reaction of heptakis-6-amino-β-cyclodextrin (the formula 1) with 8 to 40 equivalents of aminocaproic acid for which amino groups are protected by tetra-butyloxycarbonyl(Boc) groups, is carried out in reaction solvents such as a methanol/water mixed solvent at a room temperature (20° C.) for 2 to 150 hours (preferably 2 to 24 hours at the end of the reaction). Next, any deprotection (removal of Boc) reactions can preferably be performed. Those skilled in the art can properly select condensation agents and reaction solvents. As a condensation agent, the following 4-(4,6-Dimethoxy-1,3,5-triazine-2-yl)-4-methyl-morpholiniumchloride is preferred. As a reaction solvent, a methanol/water mixed solvent, in which basic compounds such as triethylamine (TEA) or N-methylmorpholine (NMM), etc., are present, is preferred.

By repeating the condensation reaction and deprotection reaction n times, CD having n aminocaproic acids as a spacer arm at all the primary hydroxy groups at position-6 in each glucopyranose that constitutes a cyclodextrin (CD) ring can be constructed. As discussed below, n is preferably an integer of 1 or 2.

Hereafter, when n=1, β-CD represented by the above formula 2 is sometimes simply referred to as "heptakis-6-amino-cap1-β-CD". When n=2, β-CD represented by the above formula 3 is sometimes simply referred to as "heptakis-6-amino-cap2-β-CD".

The spatial arrangement of folic acid in the cyclodextrin compound of the invention can be adjusted by adjusting the length of the spacer arm in order to exert two or more simultaneous interactions of two or more folic acids with the binding sites for folic acid. From the viewpoint that the spacer arm has an appropriate length and structure for exerting two or more simultaneous interactions of two or more folic acids with the binding sites for folic acid, n is preferably an integer of 1 or 2. The spacer arm has a functional group at the terminus for the condensation reaction.

In the process for production of the invention, the condensation reaction of the foregoing folic acid with the peraminated CD (the formula 1), the heptakis-6-amino-cap1-β-CD (the formula 2), or the heptakis-6-amino-cap2-β-CD (the formula 3) can be carried out to yield the desired CD compounds.

The above condensation reaction is represented by the following scheme when the heptakis-6-amino-cap2-β-CD (the formula 3) is taken as an example.

As a reaction solvent, depending on the solubility of the compound, dimethylsulfoxide (DMSO), dimethylformamide (DMF), water, methanol, isopropyl alcohol, t-butyl alcohol, N-methylpyrrolidinone (NMP), etc., can be used. Those skilled in the art can properly select condensation agents and reaction solvents.

Condensation agents that can be used in the foregoing condensation reaction include any condensation agents in the art such as 4-(4,6-dimethoxy-1,3,5-triazine-2-yl)-4-methyl-morpholiniumchloride (hereinafter, referred to as "DMT-MM"), dicyclohexylcarbodiimide (hereinafter, referred to as "DCC"), water-soluble carbodiimide (hereinafter, referred to as "WSC"), etc. Those skilled in the art can select the appropriate condensation agent according to the selected functional groups or reaction solvents. For example, when the functional group of the cyclodextrin is an amino group in the foregoing condensation reaction, the use of the condensation agent DMT-MM in the reaction of the amino group with a carboxyl group of folic acid is preferred in the view of efficiency.

DMT-MM is reacted with a carboxylic acid to yield an active ester, and then the active ester is reacted with amine to form an amide bond. There is a report that the reaction proceeds in a variety of solvents such as ethanol, methanol, i-propanol, water, etc., and proceeds quantitatively (for example, see M. Kunishima, C. Kawachi, J. Morita, K. Terao, F. Iwasaki, S. Tani, Tetrahedron, 55, 13159-13170 (1999)). Recently, attention has been focused on this point.

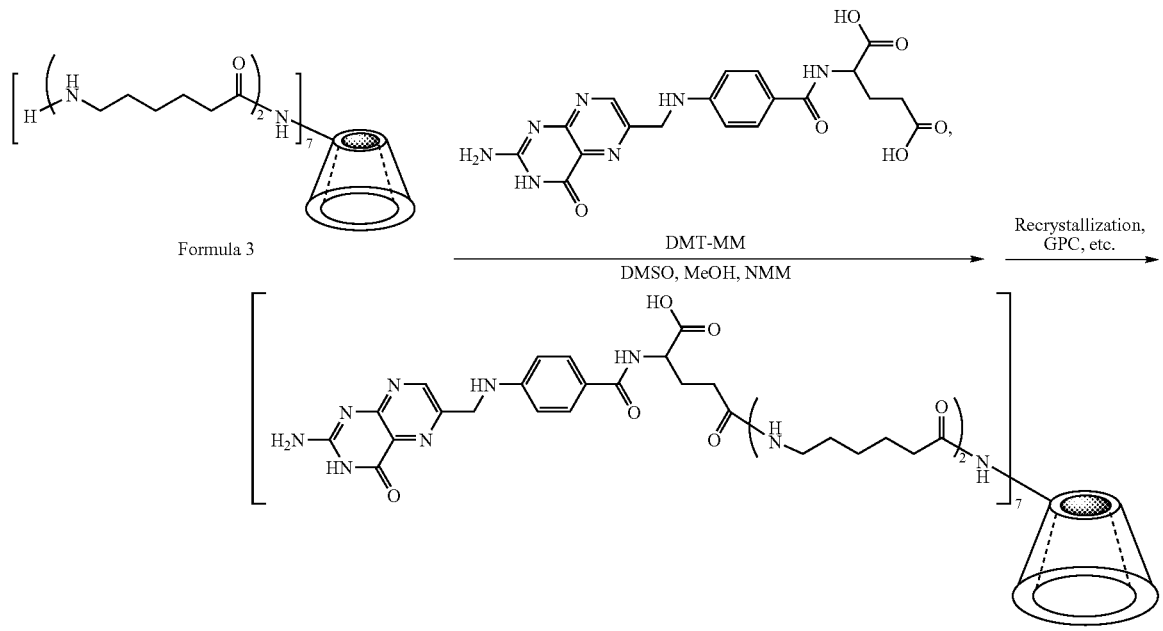

Exemplary compound 1

Specifically, relative to the peraminated cyclodextrin (CD) (the formula 1), the heptakis-6-amino-cap1-β-CD (the formula 2) or the heptakis-6-amino-cap2-β-CD (the formula 3), 10 to 100 equivalents of folic acid is dissolved in the reaction solvents. Under the presence of the basic compounds such as triethylamine (TEA) or N-methylmorpholine (NMM), etc., the reaction of the reaction solvents with the condensation agents such as 4-(4,6-Dimethoxy-1,3,5-triazine-2-yl)-4-methylmorpholiniumchloride (DMT-MM), etc., is carried out at a room temperature (30° C.) preferably for 2 to 150 hours, more preferably 12 to 60 hours.

For example, equal molar equivalents of N-methylmorpholine (NMM) or triethylamine to folic acid can be used as an agent removing hydrochloric acid. One to 5-fold molar equivalents of DMT-MM can be used as a condensation agent.

After the removal of unreacted materials by acetone reprecipitation, the product is preferred to be purified and isolated by gel permeation chromatography (GPC).

The gels that are used in GPC include Bio gel, Sephadex, TOSO-PW gel (each is a trade name) and the like. Preferred is Bio gel (e.g., P4, P6) from the perspective of the separation and purification capabilities.

Elution solvents include water, ammonia water, and the like. Preferred is water from the perspective of the capabilities of separating contaminants such as unreacted folic acids and the like.

The structure of the produced cyclodextrin compound for the given purposes can be analyzed by any methods in the art.

Next, the targeting drug delivery agents and targeting pharmaceutical compositions of the invention are described.

The targeting drug delivery agents of the invention contain the cyclodextrin compound. In particular, the targeting drug delivery agents of the invention are drug delivery agents, which contain the cyclodextrin compound having the Nanocluster effect by two or more folic acids, the agents used for a targeting drug delivery system for cancer cells, inflammation, etc. The targeting pharmaceutical compositions of the invention also contain the cyclodextrin compound and an agent. The targeting pharmaceutical compositions of the invention preferably contain equal molar equivalents of the cyclodextrin compound relative to the drug.

The targeting drug delivery agents and targeting pharmaceutical compositions of the invention may contain one of the cyclodextrin compounds, or contain two or more of the cyclodextrin compounds. When the drug coexists with the cyclodextrin compound, the drug is included (the drug-inclusion) in the cyclodextrin compound.

Here, the targeting drug delivery system (TDDS) refers to delivering the drug to the target cells selectively and topically by precisely controlling the disposition of the drug by devising a method for administering the drug (formulation, additives, etc.). According to the invention, the desired drug can be delivered selectively to the target cells or target tissues that express folate receptors. According to the invention, in particular, the desired drug can be delivered furthermore selectively to the target cells or target tissues that overexpress folate receptors. The suitable targets that are applicable to the invention include the disease tissues and disease sites of the disorders such as cancer, autoimmune diseases, inflammatory diseases, and the like.

The cancers to which the present invention is applied include epithelial malignancy, hematopoietic malignancy derived from bone marrow, etc., and particularly include ovarian cancer (non-mucinous ovarian cancer, etc.), uterine cancer, endometrial cancer, breast cancer, breast adenocarcinoma, prostate cancer, testicular cancer (testicular chorioepithelioma, etc.), brain cancer (ependymoma, etc.), throat cancer, lung cancer, lung adenocarcinoma, kidney cancer (renal cell carcinoma, etc.), liver cancer, colon cancer (colonic cancer, etc.), pleural mesothelioma, sarcoma, chronic and acute myeloid leukemia, a variety of metastatic cancers such as metastatic lung cancer, etc., and the like.

The autoimmune diseases and/or inflammatory diseases to which the present invention is applied suitably include rheumatoid arthritis, systemic lupus erythematosus, atherosclerosis, multiple sclerosis, Crohn's disease, psoriasis, ulcerative colitis, pulmonary fibrosis, graft-versus-host disease and the like.

The targeting pharmaceutical compositions of the invention can be used for the treatment of the diseases that express a folate receptor, preferably the diseases that overexpress a folate receptor in the disease tissues and disease sites. The term "treatment" is used herein in a broad sense, including not only treating or improving the diseases but also preventing or delaying the progress of the clinical condition of the disease in the mammals that may be or is affected by the diseases, and also including not only therapeutic measures but also prophylactic measures.

The drugs to which the present invention is applied can be selected properly depending on the target diseases, and the like. Preferred includes, in addition to the anticancer agents (including anticancer drugs, antimetastatic agents), protein toxins, imaging agents, antisense oligonucleotides, genes, and the like.

The targeting pharmaceutical compositions of the invention may be any of the liquid and solid agents. Specifically, the targeting pharmaceutical compositions can be injectable drugs in liquid form, particularly can be injections suitable for subcutaneous, intramuscular, intraarticular, and intravenous administration. If the targeting pharmaceutical compositions are used in liquid form, any agents that adjust pH, buffers, stabilizers, solubilizers, etc., can be added thereto, if appropriate, in addition to the drugs and the CD compounds. The targeting pharmaceutical compositions in solid form can be oral preparation such as tablets, dispersants, granules, capsules, syrup, etc., or agents for parental administration such as sprays, suppositories, injections, topical agents, intravenous infusion preparations, etc. If the targeting pharmaceutical compositions are used in solid form, any excipients, binders, disintegrants, lubricants, colorants, flavoring and odorant agents, etc., can be added thereto, if appropriate, in addition to the drugs and the CD compounds. Furthermore, various coatings such as sugar coatings, gelatin coatings, and the like may optionally be applied as needed.

The targeting pharmaceutical compositions of the invention can be administered to the mammals (preferably human) that may be or are affected by the foregoing diseases. The dosage may vary depending on the age, body weight, disease type, severity of symptoms, types of drugs, and the like of the subject. A daily dosage of from about 1 to 100 mg of the drug for an adult may be administered in a single dose or in divided doses.

The targeting drug delivery agents of the invention can preferably target the cell surface of liver parenchymal cells and can be used for liver cancer when the agents are the cyclodextrin (CD) compounds in which the glycosyl group in the substituents having the glycosyl group is a galactosyl group.

When the agents are the cyclodextrin (CD) compounds in which the glycosyl group is a fucosyl group, the agents can preferably target the cells that are localized to colon surfaces and can be used for colon cancer. When the agents are the CD compounds in which the glycosyl group in the substituents having the glycosyl group is a mannosyl group or glucosyl group, the agents can be used via macrophages for cancer.

The construction of the substituent having the glycosyl group is then described. The substituent having the glycosyl group can be constructed as the following reaction scheme when, for example, the glycoside is galactoside.

Formula 4

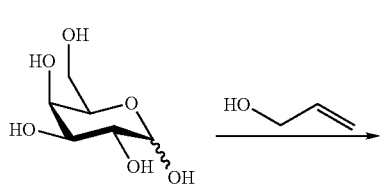

-continued

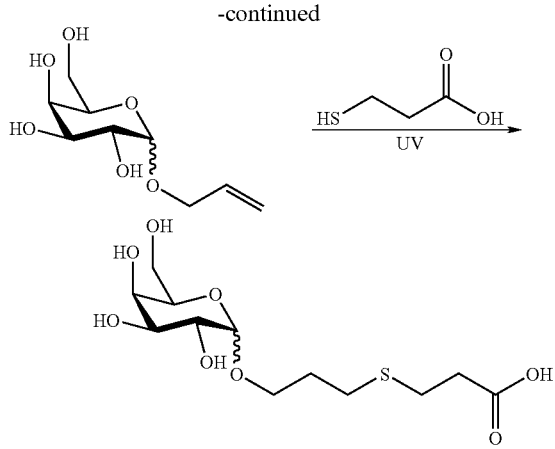

The substituent having the glycosyl group can be synthesized by a reaction of allyl alcohol with sugar or a sugar chain under the presence of acid catalysts (i.e., "oxypropenation"), and by a photoaddition reaction of mercapto fatty acids having 2-7 carbon atoms. The mercapto fatty acids are preferably 3-mercaptopropionic acid, 4-mercaptobutyric acid, etc.

Specifically, sugar or a sugar chain is dissolved in allyl alcohol, and acid catalysts are added to the solution. The solution can be heated at reflux under $N_2$ at 97° C. to yield allyl glycoside. The sugar spacer arm units can be constructed by carrying out a photoaddition reaction of the obtained allyl glycoside with mercapto fatty acids such as a 3-mercaptopropionic acid, etc.

The reaction of the allyl glycoside with a mercapto fatty acid proceeds under ultraviolet light and under an inert gas atmosphere such as a nitrogen atmosphere, argon atmosphere, and the like.

The wavelength of the ultraviolet light is in a range of 200 nm to 400 nm, preferably 340 nm to 380 nm. The irradiation time is between 1 and 20 hours, preferably between 3 and 7 hours. These can be changed properly depending on the time scale of the reaction and the reaction apparatus. For the reaction solvent, DMF, methanol, water, etc., are used.

The products can be purified by GPC on Sephadex G10.

Next, the drugs and the evaluation of the results of the association with the target proteins are described.

The drugs included into CD forms the inclusion complexes include the anticancer drug doxorubicin (DXR), etc.

The targeting pharmaceutical compositions of the invention can be targeting imaging agents; the drugs included into its cavity are labeled. Specifically, by selecting L-[3-$^{18}$F]-α-methyltyrosine ($^{18}$F-FMT) for the labeled compound with which CD forms the inclusion complexes, the compositions can be target imaging agents used in positron emission tomography (PET).

By selecting a fluorescent dye-labeled compound (e.g., fluorescein) for the labeled compound, the compositions can also be targeting imaging agents used in fluorescence endoscopy.

Furthermore, by selecting a gadolinium (Gd) compound (e.g., a gadolinium chelates aromatic compound) for the labeled compound, the compositions can be targeting imaging agents used in nuclear magnetic resonance imaging (MRI).

In addition, by selecting a barium compound, iodine, or an iodine compound (e.g., 1,3,5-triiodobenzene) for the labeled compound, the compositions can be targeting imaging agents used in X-ray computed tomography (X-ray CT).

The method for evaluating the dual recognition capabilities of the cyclodextrin (CD) compound can use the two-dimensional plot for the drug-inclusion association constant of the CD compound toward the drug versus the recognition association constant of the CD compound toward the target protein.

The surface plasmon resonance analyses can yield the association constants.

Here, the term "dual recognition" refers to recognition that the CD compounds of the invention form the inclusion complexes with the drugs in the cavity of the CD compounds, as well as associating with the target proteins via the sugar moieties.

The target proteins include a receptor protein which is present in the surface, etc. of cancer cells, and the like.

The SPR analyses using the surface plasmon resonance (SPR) optical biosensor on which the drugs such as DXR, etc., or the target proteins such as folate receptor proteins (FBP), etc. are immobilized, can yield each association constant. By using the two-dimensional plot, the CD compounds that are promising targeting drug delivery agents can be screened.

In the method for evaluating the dual recognition capabilities, each association constant of the CD compound for the drug or the corresponding cell surface receptor protein can be determined for the binding without conducting animal experiments or clinical experiments. The data can be plotted as the logarithm of one association constant versus the logarithm of the other association constant to evaluate the dual recognition capabilities. As the association constants become larger in the upper right corner, the drugs become better drug delivery agents used for the targeting drug delivery systems (TDDS) that have the superior drug-inclusion capabilities and to associate with the target proteins.

Next, the principles of the surface plasmon resonance (SPR) optical biosensor are described.

The surface plasmon resonance (SPR) method using the SPR optical biosensor (e.g., IAsys) can measure the molecular interactions of biopolymers.

Both the measurements for the associations of the CD compounds of the invention with target proteins and the measurements of the associations to form the inclusion complexes with the drugs can be conducted by the SPR method.

Specifically, the ligand (e.g., folate-binding proteins) is immobilized on a cuvette, and the analyte (e.g., the cyclodextrin (CD) compound of the invention) that is dissolved in a buffer solution is injected into the above cuvette. Evanescent wave and surface plasmon wave excite the surface plasmon when the angle of incidence on a prism is less than or equal to the angle of total reflection. The angle of incidence is measured. The angle of incidence is changed depending on the mass within the evanescent field depth of 600 nm. The amount of the changes can be observed and refers to the response (R). This angle of incidence is proportional to the mass of the adsorbed molecule. In other words, these mass changes can indicate the interaction.

The cyclodextrin compounds of the invention can form the inclusion complexes with the agents in the cavity of the cyclodextrin. In addition, the compounds exert the foregoing Nano-cluster effect by regulating a spatial concentrated arrangement of folic acid that works as a recognition tag group. The compound is superior in association with the folic acid binding sites on the target receptors of cancer cells and the like.

The sizes of the cyclodextrin compounds of the invention are, depending on the length of the side chain, less than approximately 10 nm, in many cases, is less than approximately 5 nm. The compound is also superior in cell membrane permeability and has a stable cyclodextrin ring. The cyclodextrin ring is biodegradable due to hydrolysis of the glycosidic bond, and is excellent in the safety in vivo.

The cyclodextrin compounds of the invention can have the specificity for the target organs and/or cells (e.g., cancer cells, liver, large intestine, macrophages, etc.) by further substituting the hydroxy groups in the molecule by the substituents having a variety of glycosyl groups such as a galactosyl group, a fucosyl group, and the like.

The process for producing the cyclodextrin compounds of the invention can produce the cyclodextrin compounds that have the foregoing superior characteristics without complicated processes.

The targeting drug delivery agents of the invention are less antigenic and have the characteristics of a "stealth agent" because the agents are primarily composed of cyclodextrin, which is a sugar. The term "stealth agent" herein means that the agents can move in vivo without becoming antigenic to escape from the host immune attack mediated by γ-immunoglobulin antibodies.

Since the targeting pharmaceutical compositions of the invention contain the cyclodextrin compounds, the compositions can be used as a cancer cell targeting carrier for anticancer drugs or a targeting carrier for delivering the agents to inflammatory sites, the targeting imaging agents for use in cancer tissues, the agents that deliver genes, etc., and the like.

Specifically, the compositions can be suitably used in a targeting drug delivery system for the diseases such as cancer, liver cancer, colon cancer, etc. (TDDS, a targeting drug delivery system), and suitably used as targeting imaging agents for use in cancerous tissues, etc.

EXAMPLES

Although the invention is described in more detail based on the following examples, the invention is not limited to those.

Reference Example 1

Production of heptakis-6-amino-β-CD (the Formula 1)
(1) Production of heptakis-6-chloro-β-CD 3.0274 g of β-cyclodextrin (CD) was added to a two-neck flask. After azeotropic distillation with ethanol four times, the solution was dried under vacuum (40° C.) for 20 hours. After the solution was dried under vacuum, the air in the flask was replaced by $N_2$. 2.75 g of β-CD ($2.42\times10^{-3}$ mol) was obtained. 23 ml of dimethylformamide (DMF) that was dehydrated with $CaH_2$ beforehand, was added thereto and was dissolved. The resultant mixture was stirred under a nitrogen atmosphere. In addition, 2.9 ml ($37\times10^{-3}$ mol) of methanesulfonyl chloride was added dropwise to the mixture. Then, the reaction was carried out in an oil bath at a temperature of 80° C. for 4 hours and 30 minutes. After the reaction was cooled to room temperature, 5 ml of ethanol was added to the mixture to stop the reaction. The mixture was stirred for 30 minutes. The mixture was neutralized (pH 7-8) with 12 ml of a methanol solution containing 28% sodium methoxide, and stirred for 16 hours and 20 minutes.

The mixture was concentrated and dried in an evaporator, and the product was washed with methanol and water after the product was transferred to a Buechner funnel. After the product was dried in a vacuum (at 40° C.) for 24 hours and 20 minutes, the product (2.5886 g, yield 85%) was obtained. The product was analyzed by thin layer chromatography (TLC) and laser ionization time-of-flight mass spectrometry (MALDI-TOF MS). TLC using a developing solvent (1-butanol:ethanol:water=5:4:3) and a color agent, anisaldehyde, showed a value of 0.83.

(2) Production of heptakis-6-azido-β-CD 1.2630 g ($9.9930\times10^{-4}$ mol) of heptakis-6-chloro-β-CD was dissolved in a solution (dimethylacetamide(DMAc):Water=60 ml: 8 ml) in a recovery flask, and 1.4232 g ($218.9\times10^{-4}$ mol) of sodium azide was added to the solution. After the reaction was carried out in an oil bath at a temperature of 110° C. for 24 hours, the reaction solution was stirred for 1 hour until the reaction was cooled to room temperature. The reaction solution was added dropwise with a pipette to 700 ml of water, and the product was precipitated. The filtrates that were impurities were removed. The residue was washed with water after transferred to a Buechner funnel. After the product was dried in a vacuum (40° C.) for 13 hours, the product (1.1562 g, yield 88%) was obtained. The product was analyzed by thin layer chromatography (TLC) and laser ionization time-of-flight mass spectrometry (MALDI-TOF MS). TLC using a developing solvent (1-butanol:ethanol:water=5:4:3) and a color agent, anisaldehyde, showed a Rf value of 0.77.

(3) Production of heptakis-6-amino-β-CD (the Formula 1)

1.0015 g ($7.6446\times10^{-4}$ mol) of heptakis-6-azido-β-CD and 3.1962 g ($121.86\times10^{-4}$ mol) of triphenylphosphine were dissolved in 73 ml of DMAc. After the reaction was carried out at room temperature for 1 hour, 30 ml ($4000\times10^{-4}$ mol) of 25% ammonia water was added to the reaction solution, and the reaction solution was stirred for 22 hours and 30 minutes. After the reaction, the reaction solution was concentrated in an evaporator. The product was precipitated by adding 500 ml of ethanol, and the filtrates that were impurities were removed. The residue was washed with ethanol after transferred to a Buechner funnel. After the product wad dried in a vacuum (40° C.) for 19 hours and 50 minutes, the product (0.8321 g, yield 96%) was obtained. The product was analyzed by thin layer chromatography (TLC) and laser ionization time-of-flight mass spectrometry (MALDI-TOF MS). TLC used a developing solvent (1-butanol:ethanol:water=5:4:3) and color agents containing anisaldehyde and ninhydrin.

Reference Example 2

Production of heptakis-6-amino-cap1-β-CD (the Formula 2)

To introduce aminocaproic acid into heptakis-6-amino-β-CD (the formula 1), N-methylmorpholine (NMM) (10 equivalents, 1.67 ml) and the heptakis-6-amino-β-CD (1.71 g) were added to a methanol/water mixture (1:1 v/v, 20 ml: 20 ml) together with aminocaproic acid (10 equivalents, 3.51 g) in which an amino group was protected by a Boc group. A condensing agent (DMT-MM) (10 equivalents, 4.2 g) was then added at one time, was reacted with the mixture at room temperature for 48 hours. After the reaction, the solution was concentrated in an evaporator. The product was reprecipitated by pure water. After the filtrates were removed, the residue was dissolved into methanol and dried to yield heptakis-6-Boc-amino-cap1-β-CD.

To the heptakis-6-Boc-amino-cap1-β-CD was added approximately 4 ml of 4 M HCl/dioxane solution, and the solution was stirred on ice for 3 hours, which resulted in the removal of Boc. Then, heptakis-6-amino-cap1-β-CD (the formula 2) was obtained. The product (2.17 g, yield 74.6%) was obtained. The product was analyzed by MALDI-TOF MS.

MALDI-TOF MS: calcd for 1920.55 [M]$^+$, 1943.54 [M+Na]$^+$, 1959.65 [M+K]$^+$. found: m/z 1919.50, 1956.81.

Reference Example 3

Production of heptakis-6-amino-cap2-β-CD (the Formula 3)

To further introduce aminocaproic acid into the heptakis-6-amino-cap1-β-CD, NMM (20 equivalents, 1.15 ml) and the heptakis-6-amino-cap1-β-CD (1.0 g) were added to the methanol solvent (100 ml) together with aminocaproic acid (20 equivalents, 2.4 g) in which an amino group was protected by a Boc group. DMT-MM (20 equivalents, 2.88 g) was then added at one time, was reacted with the mixture at room temperature for 48 hours. After the reaction, the solution was concentrated in an evaporator. The product was reprecipitated by pure water. After the filtrates were removed, the residue was dissolved into methanol and dried to yield heptakis-6-Boc-amino-cap2-β-CD.

To the heptakis-6-Boc-amino-cap2-β-CD was added approximately 4 ml of 4 M HCl/dioxane solution, and the solution was stirred on ice for 3 hours, which resulted in the removal of Boc. Then, heptakis-6-amino-cap2-β-CD (the formula 3) was obtained. The product (1.46 g, yield 103.4%) was obtained. The product was analyzed by MALDI-TOF MS.

MALDI-TOF MS: calcd for 2712.3 $[M]^+$, 2735.29 $[M+Na]$, 2751.4 $[M+K]^+$. found: m/z 2711.45, 2732.78, 2748.80.

Example 1

Production of the Exemplary Compounds 1 and 7-10

To a 100-ml reaction container was added 53.3 mg ($2\times10^{-5}$ mol) of heptakis-6-amino-cap2-β-CD (the formula 3) and 276.9 mg ($60\times10^{-5}$ mol) of folic acid. The mixture was dissolved in 20 ml of DMSO at 100° C. 66 μl ($60\times10^{-5}$ mol) of NMM, DMT-MM ($60\times10^{-5}$ mol), and 20 ml of methanol were then added to the mixture, and the mixture was stirred in an oil bath at 30° C. for 45 hours.

(a) After the reaction, the mixture was reprecipitated by acetone, and the precipitate was collected by suction filtration. The residue was dissolved with 1 M ammonia water into a recovery flask and lyophilized to dryness. The purification was performed by GPC on Bio-Gel-P6. GPC column conditions were as follows: φ 4 cm×92 cm, elution rate 0.25 ml/min, sample concentration 294 mg/4 ml of ammonia water. After GPC on Bio-Gel-P6, the product (55.5 mg, yield 49.8%) was obtained.

After the purification of the (a), the product was measured by NMR. Each multiplet signal (δ ppm: 8.66-8.69, 7.61-7.70, 6.60-6.71) was composed of the signals of a folic acid moiety of the exemplary compound 1 and the signals of unreacted folic acid that was a contaminant. The degree of substitution was estimated by the calculation of the integral value of each signal to average 6.4 folic acids per the compound. The results indicated that the product coexisted with a trace of a compound in which one of the folic acids of the exemplary compound 1 was removed from the exemplary compound 1 (a cyclodextrin compound with 6 substitutions each having folic acid). The exemplary compound 1 was then purified by the following purification procedure (b).

(b) After the reaction, the mixture was reprecipitated by acetone, and the precipitate was collected by suction filtration. The residue was evaporated to dryness in a rotary evaporator to remove volatile constituents. 100 mg of the residue was dispersed in water by sonication, and was heated to 50-60° C. Insoluble materials were filtered on a membrane filter (0.45-μm polypropylene filter, manufactured by Whatman, Japan) and GPC was performed on Bio-Gel-P4 on a glass column of φ 4 cm×60 cm at a flow rate of 2.0 ml/min under pressure of 17 atm, using water as an eluent. Fractions were collected by a fraction collector, dried in an evaporator, dissolved into a small amount of water, and lyophilized to dryness to yield the exemplary compound 1 (18.3 mg, yield 44.4%).

In addition, the exemplary compounds 7-10 were obtained at the same time, and each was isolated.

The exemplary compounds 1 and 7-10 were analyzed by TLC (Rf value 0.48; a developing solvent, 1-butanol:ethanol: water: 25% ammonia water=5:4:3:5; color agents: anisaldehyde and iodine); MALDI-TOF MS (M=$C_{259}H_{350}O_{77}N_{70}$; $[M+H]^+$: calcd for 5676.98, found: 5674.10; $[M+Na]^+$: calcd for 5698.96, found: 5697.97; $[M+K]^+$: calcd for 5715.07, found: 5716.21). $^1$H NMR and $^1$H-$^1$H COSY were employed, and the peaks were attributed to the compounds.

$^1$H NMR (500 MHz, DMSO-$D_2$O) δ ppm: 1.24 (28H, s), 1.40 (28H, s), 1.49 (28H, s), 1.93-1.97 (14H, m), 2.06 (28H, s), 2.26-2.28 (14H, t), 3.03 (28H, s), 4.20 (7H, t), 4.53 (14H, s), 4.86 (7H, s), 6.60-6.71 (14H, m), 7.61-7.70 (14H, m), 8.66-8.69 (7H, m). The melting points were determined by a conventional melting-point apparatus, and the compounds were melted at 188-189° C.

The exemplary compound 7: calcd for 5812.12 $[M+Na]^+$; found: 5812.03 $[M+Na]^+$.

The exemplary compound 8: calcd for 5585.81 $[M+Na]^+$; found: 5586.03 $[M+Na]^+$.

The exemplary compound 9: calcd for 5275.58 $[M+Na]^+$; found: 5275.40 $[M+Na]^+$.

The exemplary compound 10: calcd for 5065.37 $[M+K]^+$; found: 5065.27 $[M+K]^+$.

Example 2

Production of the Exemplary Compounds 2 and 6

(1) Production of 1-D-galactosyl-oxypropene 5.0138 g of galactose was added to a two-neck flask. After azeotropic distillation with ethanol four times, the solution was dried under vacuum. The air in the flask was replaced by $N_2$, and the pellet was dissolved into 50 ml of allyl alcohol under $N_2$ atmosphere. 1.5091 g of Dowex 50W-X8 was added thereto as an acid catalyst, and the mixture was heated under reflux for 2 hours. The Dowex 50W-X8 was then removed by suction filtration. The mixture was transferred to a two-neck flask, and evaporated to dryness. After lyophilization, the product (6.22 g, crude yield 101%) was obtained.

(2) Production of 1-α-D-galactosyl-oxypropylthioethyl-carboxylic Acid (the Formula 4)

In a two-neck flask, 6.22 g of 1-D-galactosyl-oxypropene was dissolved into 25 ml of methanol under an argon atmosphere. 2.7 ml of 3-mercaptopropionic acid was then added thereto. An argon airflow was stopped. A lid was placed on the flask, and the mixture was stirred under UV irradiation for 5 hours.

After concentrated to dryness, the mixture was lyophilized to dryness. The purification was performed by GPC on Sephadex G-10. The product (7.06 g, yield 77%) was obtained.

Calcd for 349.35 $[M+Na]^+$, 365.46 $[M+K]^+$; found: 350.04, 365.97.

(3) Production of the Exemplary Compounds 2 and 5

4.5 mg of the heptakis-6-amino-β-CD (produced in Reference Example 1) and 1.8 mg of folic acid (1 equivalent for the heptakis-6-amino-β-CD) were dissolved into 1.0 ml of methanol and 1.0 ml of DMSO (1:1). A condensing agent DMT-MM (1 equivalent for the heptakis-6-amino-β-CD) was added to the solution. The reaction was carried out, and the reaction mixture was stirred at room temperature for 30 minutes. 39.6 g of D-galactosyl-oxypropylthioethylcarboxylic acid (30 equivalents for the heptakis-6-amino-β-CD) was dissolved in 0.5 ml of methanol. A condensation agent DMT-MM (30 equivalents for the heptakis-6-amino-β-CD) was added to the solution. The reaction was carried out, and the reaction mixture was stirred at room temperature for 13 days. A total of 34.7 mg of DMT-MM was used.

After analyzed by MALDI-TOF MS, the products were added dropwise with a Pasteur pipette to 10 volumes of an acetone solution. The products and unreacted folic acid were precipitated. After the precipitates were collected by suction filtration, the constituents (from the precipitated substance) that were soluble in water were transferred to a recovery flask, and lyophilized to dryness. The products (10.5 mg, yield 76%) were obtained as a mixture composed of the exemplary compounds 2 and 5.

The exemplary compound 2 ($C_{147}H_{208}O_{71}N_{28}S_4$) calcd for 3670.73 $[M+K]^+$; found: 3671.04 $[M+K]^+$.

The exemplary compound 5 ($C_{133}H_{214}O_{75}N_{14}S_6$) calcd for 3440.66 $[M+K]^+$; found: 3432.68 $[M+K]^+$.

As described, different peaks were observed by the MS spectroscopy, etc., and the elution time on GPC varied depending on the size of the molecule. Thus, each of the exemplary compounds 2 and 5 was isolated and purified by a conventional GPC on Bio-Gel-P4.

Example 3

Production of the Exemplary Compounds 3 and 6
(1) Production of 1-L-fucosyl-oxypropylthioethylcarboxylic Acid According to the procedure similar to the procedure of producing the foregoing 1-D-galactosyl-oxypropylthioethylcarboxylic acid (the formula 4), 1-L-fucosyl-oxypropylthioethylcarboxylic acid was produced.

Calcd for 333.35 $[M+Na]^+$, 349.46 $[M+K]^+$; found: 334.09 $[M+Na]^+$, 350.08 $[M+K]^+$.

(2) Production of the Exemplary Compounds 3 and 6

Next, 118.8 mg ($3.82 \times 10^{-4}$ mol) of the 1-L-fucosyl-oxypropylthioethylcarboxylic acid and 157.5 mg ($3.56 \times 10^{-4}$ mol) of folic acid was added to a 100-ml container, and were dissolved in 6 ml of DMSO. 13.6 mg ($1.20 \times 10^{-5}$ mol) of the heptakis-6-amino-β-CD that was produced in the Reference Example 1, 201.3 mg of DMT-MM, and 12 ml of methanol were added thereto, and the mixture was stirred for 13 days. Then, the mixture was reprecipitated by acetone, and 1-L-fucosyl-oxypropylthioethylcarboxylic acid, folic acid, and DMT-MM were removed by suction filtration. The constituents that were soluble in water were transferred to a recovery flask (ultrapure water was used when the residue on the glass filter was transferred to a recovery flask), and evaporated to dryness. The products (11.1 mg, yield 26.8%) were obtained as a mixture composed of the exemplary compounds 3 and 6.

The exemplary compound 3 ($C_{140}H_{211}O_{68}N_{21}S_5$) calcd for 3475.70 $[M+K]^+$; found: 3478.85 $[M+K]^+$.

The exemplary compound 6 ($C_{133}H_{214}O_{69}N_{14}S_6$) calcd for 3344.66 $[M+K]^+$; found: 3347.65 $[M+K]^+$.

As described, different peaks were observed by the MS spectroscopy, etc., and the elution time on GPC varied depending on the size of the molecule. Thus, each of the exemplary compounds 3 and 6 was isolated and purified by a conventional GPC on Bio-Gel-P4.

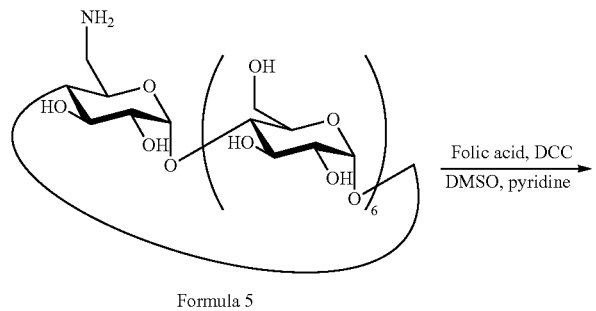

Formula 5

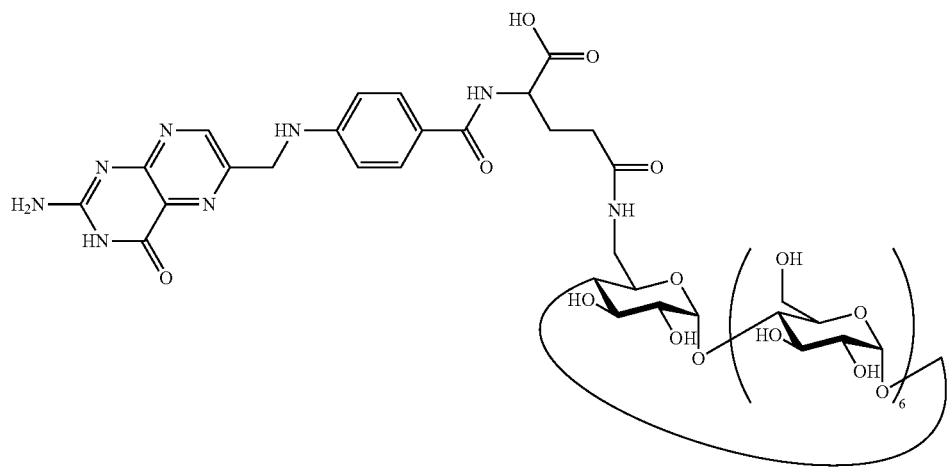

Exemplary compound 4

Example 4

Production of the Exemplary Compound 4

Mono-6-amino-β-CD (the formula 5; 0.17 g) that was synthesized by a known method (for example, Aoki, R. Arai, K. Hattori, J. Inclusion Phenom., 50, 115-120 (2004)), folic acid (0.07 g), and dicyclohexylcarbodiimide(DCC; 0.03 g) were dissolved in 5 ml of DMSO and 10 μL of pyridine, and the mixture was stirred at room temperature (24° C.) for 24 hours. After the reaction, the mixture was concentrated in an evaporator, and the purification was performed by GPC on Sephadex G-10 column (3 cm×20 cm). The collected solution was evaporated to dryness, dissolved into a small amount of water, and lyophilized to dryness to yield the exemplary compound 4. The product (0.11 g, yield 45%) was obtained.

$^1$H NMR (500 MHz, D$_2$O) δ ppm: 1.80-2.32 (4H, m), 4.95-5.00 (7H, d), 6.72-6.76 (2H, d), 7.53-7.57 (2H, d); MALDI-TOF MS (C$_{61}$H$_{89}$O$_{39}$N$_8$) calcd for 1558.39 [M+H]$^+$; found: 1559.13 [M+H]$^+$.

Example 5

Evaluation of the Association of Folate Binding Proteins (FBP) with the Exemplary Compound 1 and the Like <Immobilization of FBP>

The reagents used for immobilization were obtained as follows:

1 mM BS$^3$ solution: 2.9 mg of Bis(sulfosuccinimidyl) suberate (BS$^3$) was dissolved into 5 ml of 10 mM phosphate buffer solution (pH 7.2);

a solution used for immobilization of FBP: 1 mg of FBP (manufactured by SIGMA) was dissolved into 1 ml of 10 mM phosphate buffer solution (pH 7.2).

The FBP was immobilized on a cuvette, and the following procedures (1)-(8) using the IAsys (a surface plasmon resonance (SPR) apparatus) were used.

(1) As a linker with which an aminosilane group on the surface of SPR optical biosensor cuvette and an amino group of lectins was reacted, 1 mM of the BS$^3$ solution was injected into the cuvette. The reaction was carried out beforehand. The solution was incubated in the cuvette for 15 minutes until the response reaches equilibrium.

(2) 10 mM phosphate buffer solution (pH 7.2) was injected into the cuvette, and we waited until the response value became constant.

(3) The step (1) and (2) were repeated one or more times (e.g. 4 times) until the fluctuations in the response value were small.

(4) An acetic anhydride-acetic acid solution (volume ratio 1:1) was injected into the cuvette to deactivate any remaining aminosilane groups and to block these.

(5) For cleaning, 10 mM phosphate buffer solution (pH 7.2) was injected into the cuvette. 10 mM phosphate buffer solution (pH 7.2) was again injected into the cuvette to replace the solvent.

(6) The solution used for the immobilization of FBP was injected into the cuvette, and the reaction was carried out. The incubation continued until equilibrium was reached.

(7) 10 mM phosphate buffer solution (pH 7.2) was injected in the cuvette, and we waited until the response value became constant.

(8) Considering the background effects on the cuvette, we injected 1 M ethanolamine solution into the cuvette to deactivate any remaining succinimidyl ester groups at the end of BS$^3$ and to block these.

The amount of change in response of FBP at the injection step (6) was 1081.4 arc sec. Thus, FBP was immobilized at 1.80 ng/mm$^2$ (when R=600 arc sec, the surface protein concentration was 1 ng/mm$^2$. So, one aminosilane group was present within 1 nm$^2$).

<Evaluation of Association of the Exemplary Compound 1 and the Like with FBP>

To a cuvette on which FBP was immobilized was added 200 μl of the exemplary compound 1 (1.0×10$^{-6}$ M) that was dissolved in 10 mM phosphate buffer solution (pH 7.3; containing 0.85% NaCl). A saturation curve shown in FIG. 1 was obtained (measured at a temperature of 25.0° C.). The mixture composed of the exemplary compounds 2 and 5 obtained in Example 2, the mixture composed of the exemplary compounds 3 and 6 obtained in Example 3, as comparative examples, the comparative compounds 1 and 2, and unmodified β-CD, were independently analyzed by the SPR method. Each molecule had the concentration of 1.0×10$^{-6}$ M. A method similar to the method measuring the exemplary compound 1, was used. The association characteristics of each compound that bound to FBP were evaluated.

Comparative compound 1:

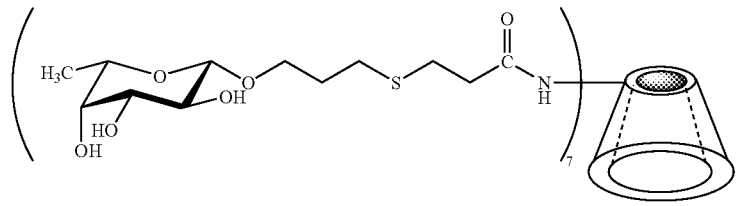

Comparative compound 2:

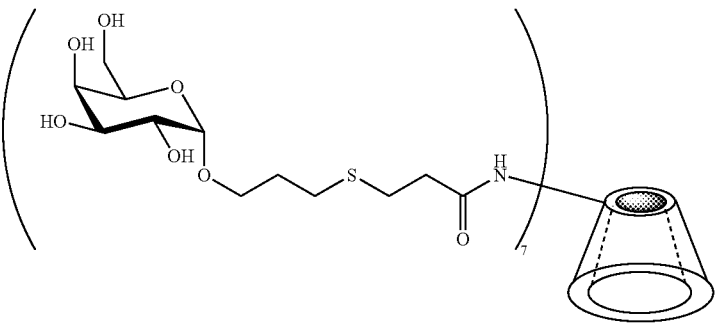

FIG. 1 is a diagram showing the results of the SPR measurements that indicated the interaction of the exemplary compound 1 (1), the mixture composed of the exemplary compound 2 and 5 (2), the mixture composed of the exemplary compound 3 and 6 (3), as a comparative example, the comparative compound 1 (4), the comparative compound 2 (5), or unmodified β-CD (6) with FBP.

Since the amount of change of the response is proportional to the mass of the interacted compound, the association constant increases with increasing response. This means that the compound has superior association characteristics.

FIG. 1 clearly demonstrated that the comparative compounds 1 and 2, and unmodified β-CD not having folic acid, which works as a recognition tag group, did not exhibit any interaction properties. On the other hand, both the mixture composed of the exemplary compound 2 and 5 and the mixture composed of the exemplary compound 3 and 6 exhibited the association characteristics for FBP. In addition, the exemplary compound 1 having 7 substituents each having folic acid interacted most strongly with FBP because of the above Nano-cluster effect. The association constant was $5.1 \times 10^9$ $M^{-1}$.

In addition, the similar SPR measurements were carried out on the exemplary compound 4. The results showed the weak interaction compared to the exemplary compound 1 having 7 substituents each having folic acid. The association constant was estimated to be $7.8 \times 10^5 M^1$.

Example 6

Comparative evaluation of the interaction of the exemplary compound 1 with CaCo-2 tumor cells or normal rat liver cells.

The SPR measurements of the exemplary compound 1 that bound to human colon cancer-derived Caco-2 cells and, as comparative target cells, normal rat liver cells were conducted by using the similar foregoing procedures. Each interaction was evaluated comparatively.

Experiment 6-1: The SPR measurements of the interaction with Caco-2 tumor cells The immobilization of Caco-2 cells was performed by the procedures similar to those of Example 5 <Immobilization of FBP>. Instead of using the solution that was used for the immobilization of FBP, the solution containing a suitable amount and concentration of the solution (phosphate buffer solution (pH 7.3)+0.85% NaCl) (manufactured by CORNING) containing Caco-2 cells was used as a fixative. In addition, to the Caco-2 cells-immobilized cuvette was added 200 µl of the exemplary compound 1 ($1.0 \times 10^{-10}$ M) that was dissolved in the phosphate buffer solution (pH 7.3)+ 0.85% NaCl. The SPR measurements were then carried out.

Experiment 6-2: The SPR measurements of the interaction with normal rat liver cells The immobilization of normal rat liver cells was performed by the procedures similar to those of Example 5 <Immobilization of FBP>. Instead of using the solution that was used for the immobilization of FBP, the solution containing a suitable amount and concentration of the solution (saline solution) (manufactured by Cosmo Bio. (RKL)) containing normal rat liver cells was used as a fixative. In addition, to the normal rat liver cells-immobilized cuvette was added 200 µl of the exemplary compound 1 ($1.0 \times 10^{-4}$ M) that was dissolved in the saline solution (containing 1 mM $CaCl_2$ and NaCl). The SPR measurements were then carried out.

Figure 2:
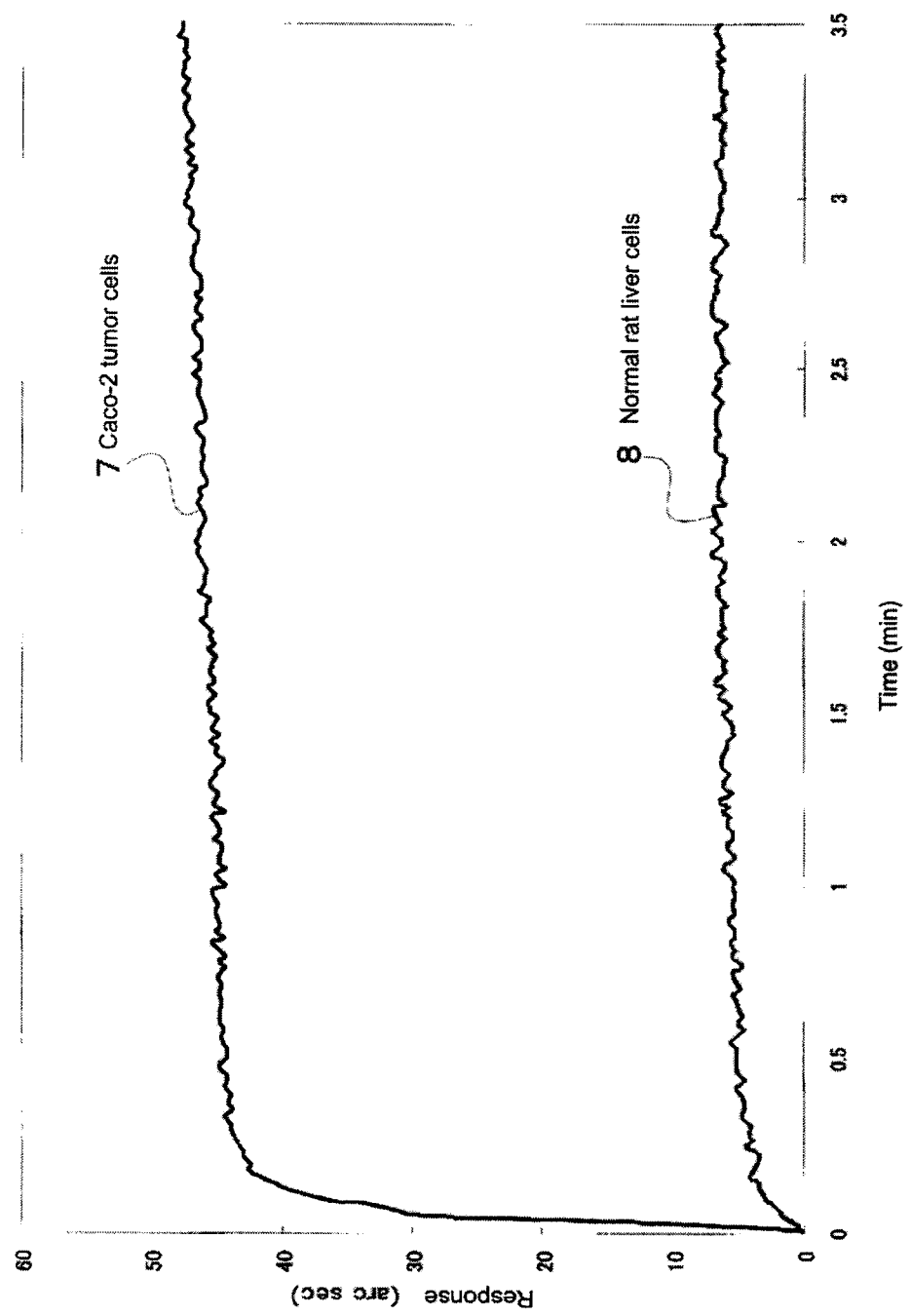
FIG. 2 is a diagram showing the results of the SPR measurements, indicating the interaction properties of the exemplary compound 1 for Caco-2 human colon cancer cells or normal rat liver cells.

FIG. 2 showed the results of experiment 6-1 and 6-2. FIG. 2 is a diagram showing the results of the SPR measurements indicating the interaction of the exemplary compound 1 with Caco-2 tumor cells (7) or normal rat liver cells (8).

As described above, the association constant increases with increasing response. This means that the compound has superior association characteristics. FIG. 2 showed that the exemplary compound 1 had little interaction with the normal rat liver cells but interacted strongly with the Caco-2 tumor cells. The results indicated that the compound specifically interacted with cancer cells.

Example 7

Evaluation of the interaction of the exemplary compound 1 with Caco-2 tumor cells or the anticancer agent, DXR The interaction was evaluated by the method using human colon cancer-derived Caco-2 cells.

Experiment 7-1: The measurements of the interaction with Caco-2 tumor cells The immobilization of Caco-2 cells was performed by the procedures similar to those of Example 5 <Immobilization of FBP>. Instead of using the solution that was used for the immobilization of FBP, the solution containing a suitable amount and concentration of the solution (phosphate buffer solution (pH 7.3)+0.85% NaCl) (manufactured by CORNING) containing Caco-2 cells was used as a fixative. To determine the association constant by a liner plot, the solution containing varied concentrations of the exemplary compound 1 was injected in the Caco-2 cells-immobilized cuvette. The SPR measurements were then carried out.

Figure 3:
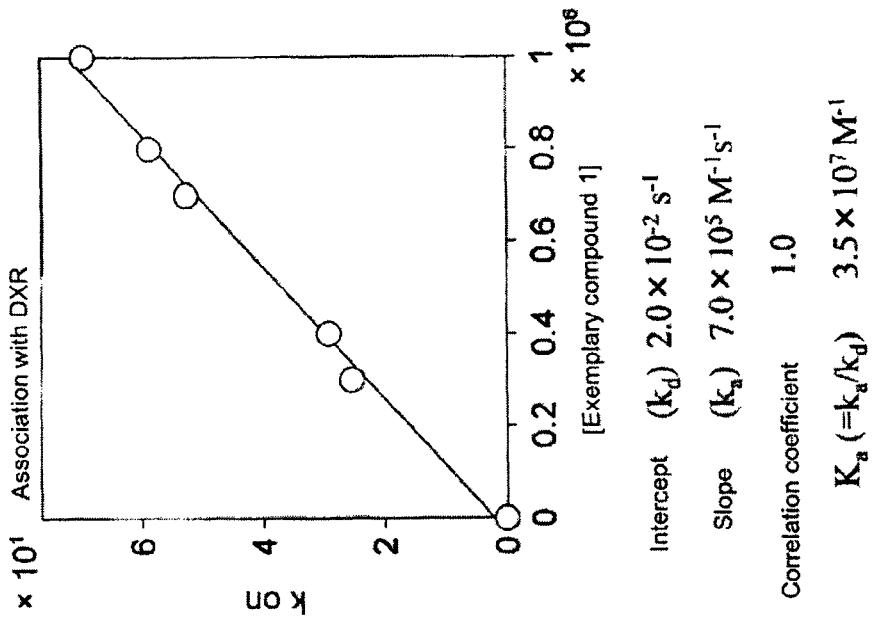
FIG. 3a is a linear plot showing a kinetic behavior of the interaction of the exemplary compound 1 with Caco-2 tumor cells.
FIG. 3b is a linear plot showing a kinetic behavior of the interaction of the exemplary compound 1 with an anticancer drug, DXR.
Figure 3:
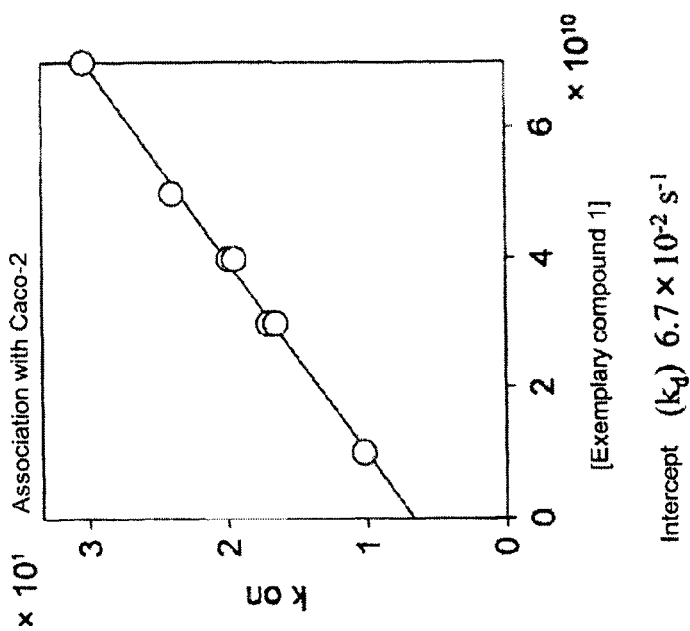

FIG. 3a is a linear plot showing the kinetic behavior of the interaction of the exemplary compound 1 with Caco-2 cells.

FIG. 3a clearly showed that the association constant of the exemplary compound 1 was $5.1 \times 10^9$ $M^{-1}$ when the results of the measurements of the interaction with Caco-2 cells were analyzed.

The association constant of the antigen-antibody reaction, which is a typical example of specific reactions, is approximately $10^{10}$ $M^{-1}$. The results showed that the association constant of the exemplary compound 1 for Caco-2 cells was approximately equal to that of the above reaction. Therefore, the results indicated that the interaction between the exemplary compound 1 and cancer cells was sufficiently specific. This strong interaction was due to the above Nano-cluster effect.

Experiment 7-2: Measurements of the capabilities of the compounds that formed the inclusion complexes with an agent, DXR The capabilities of the CD compound of the invention were evaluated by the procedures similar to those of Experiment 7-1. An anticancer and antibiotic agent, doxorubicin (hereafter, referred to as "DXR") was used as a drug.

1) Immobilization of DXR

Immobilization of DXR on the surface of an optical biosensor cuvette was performed by using the procedures similar to those of the above immobilization of FBP. A buffer with a different pH was used as a solvent for drugs.

An aminosilane group on the surface of the cuvette was reacted with a linker. 1 mM of the $BS^3$ solution/10 mM of phosphate buffer solution (pH 6.5) was used for the reaction. Then, an amino group of DXR was reacted with the other side of $BS^3$ linker. The steps were repeated one or more times until the response value became constant. An acetic anhydride-acetic acid solution (volume ratio 1:1) was injected into the cuvette to deactivate any remaining aminosilane groups and to block these. After the blocking, the solution was replaced by 10 mM acetic buffer (pH 5.3). The DXR solution (2 mg DXR/10 mM acetic buffer (pH5.3)) was added thereto. The reaction was carried out. Considering the background effects on the cuvette, we then injected 1 M ethanolamine solution (pH 8.5) into the cuvette to block succinimidyl ester groups.

The amount of change in response of DXR was 186.1 arc sec. Thus, DXR was immobilized at 0.31 ng/mm² (when R=600 arc sec, the surface protein concentration was 1 ng/mm². So, one aminosilane group was present within 1 $nm^2$).

2) Measurements

The kinetic behavior of the interaction of the exemplary compound 1 with DXR was measured by the procedures similar to those of Experiment 1. The DXR-immobilized cuvette described above was used. FIG. 3b showed the results. FIG. 3b is a linear plot showing the kinetic behavior of the interaction of the exemplary compound 1 with DXR.

The linear plot shown in FIG. 3b clearly showed that the association constant of the exemplary compound 1 for DXR was $3.5 \times 10^7$ $M^{-1}$. It is known that when the association constant is more than $10^6$ $M^{-1}$, the drugs can be used as a drug delivery agent. We observed that the association constant was larger than that of the above case. This was due to the strong Sea anemone effect (see, K. Hattori, A. Kenmoku, T. Mizuguchi, D. Ikeda, M. Mizuno, T. Inazu, J. Inclusion Phenom. Macrocyclic Chemistry, 56, 9-16 (2006)), when DXR was included, because the folic acid moieties were hydrophobic.

In addition, the association constant of the exemplary compound 4 for anticancer drug DXR was determined by the method similar to that of the exemplary compound 1. The association constant of the exemplary compound 4 for DXR was smaller than that of the exemplary compound 1 having 7 substituents each having folic acid, and was $1.72 \times 10^5$ $M^{-1}$.

The following comparative compound 3 which was produced by substituting one of hydroxy groups at position-3 in a glucopyranose that constitutes cyclodextrin by a substituent having folic acid, was used in the experiments to determine the association constant of the compound for Caco-2 cells or DXR.

The results, in addition to the results of the exemplary compound 1 and 4, were shown in the following table 1.

for a targeting drug delivery system for cancer cells because the compounds showed the dual recognition capabilities for both cancer cells and drugs.

INDUSTRIAL APPLICABILITY

The cyclodextrin compounds of the invention can be used as a cancer cell targeting carrier for anticancer drugs or a targeting carrier for delivering agents to inflammation sites, a targeting imaging agent for cancer tissues, and an agent for delivering genes.

The targeting drug delivery agents and targeting pharmaceutical compositions of the invention can preferably be used in a targeting drug delivery system (TDDS) for the diseases such as cancer, liver cancer, colon cancer, and the like. These can also preferably be used as a targeting imaging agent for the diseases such as cancer, liver cancer, colon cancer, and the like.

Although the inventor illustrates the invention with the embodiments, the inventor does not intend to limit the invention in any details herein unless otherwise stated. The invention should be interpreted broadly in accordance with the sprit and scope of the disclosed invention.

The present application claims the benefit of Japanese Patent Application No. 2007-256527, filed on Sep. 28, 2007, incorporated herein by reference in its entirety for all purposes.

TABLE 1

Comparative compound 3:

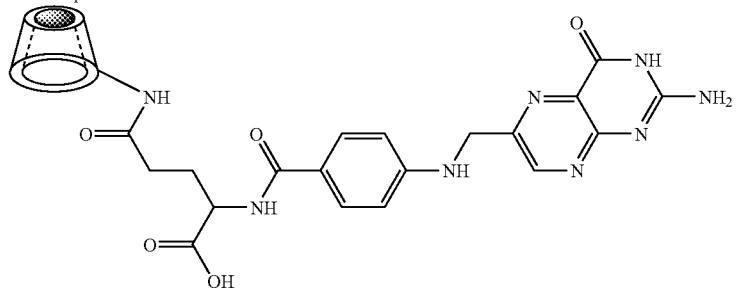

| Compound | Receptor | Association constant Ka ($M^{-1}$) | Drug | Association constant Ka ($M^{-1}$) |
|---|---|---|---|---|
| Exemplary Compound 1 | Caco-2 | $5.1 \times 10^9$ | DXR | $3.5 \times 10^7$ |
| Exemplary Compound 4 | FBP | $7.8 \times 10^5$ | DXR | $1.7 \times 10^5$ |
| Comparative Compound 3 | Caco-2 | $1.8 \times 10^4$ | DXR | $2.5 \times 10^3$ |

The results shown in Table 1 clearly indicated that the exemplary compound 1 having 7 substituents each having folic acid is approximately $10^4$-fold higher in capabilities to associate with receptors than the exemplary compound 4 or the comparative compound 3. On the other hand, it was indicated that the exemplary compound 1 having 7 substituents each having folic acid exhibited more than $10^2$-fold higher capabilities, by which the compound formed the inclusion complexes with DXR, than the exemplary compound 4 or the comparative compound 3 due to the above Sea anemone effect.

The above results suggested that the cyclodextrin compounds of the invention could be used as a delivery agent used

What is claimed is:

1. A cyclodextrin compound, wherein the compound is represented by the general formula 1:

General formula 1

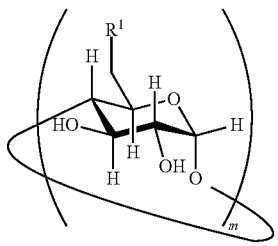

wherein m represents an integer of 6 to 8;

each R 1 is independently selected from a substituent having folic acid, a hydroxy group or a substituent having a glycosyl group;

the number of the substituent having folic acid is at least two in the cyclodextrin compound; and the substituent having folic acid is represented by the general formula 2:

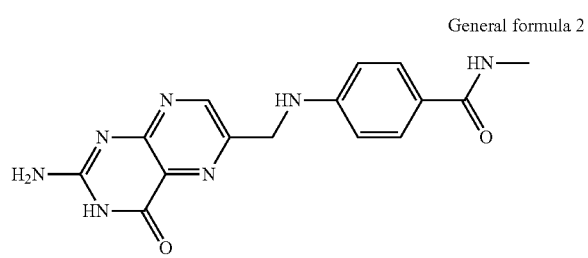

General formula 2

-continued

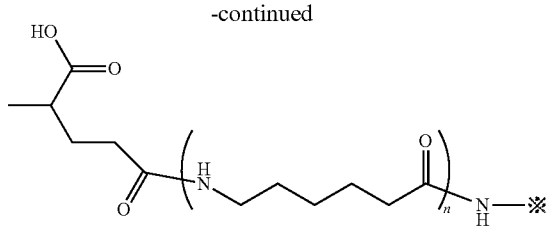

wherein the "✳" represents a binding position with a carbon atom at position-6 in the glucopyranose constituting the cyclodextrin;

n represents an integer of 0 to 3; and when n=0, a portion between a carbonyl carbon atom and an amino nitrogen atom represents a single bond.

2. The cyclodextrin compound of claim 1, wherein the number of the substituent having folic acid is at least seven in the cyclodextrin compound.

3. The cyclodextrin compound of claim 1, wherein the compound is represented by any one of the formulae

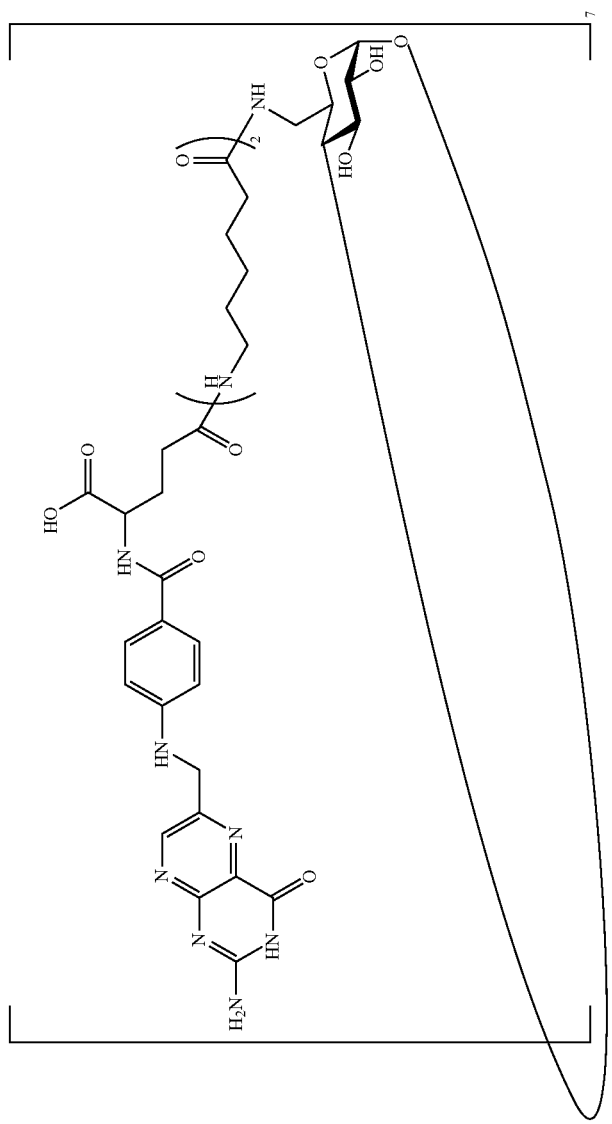
Exemplary compound 1

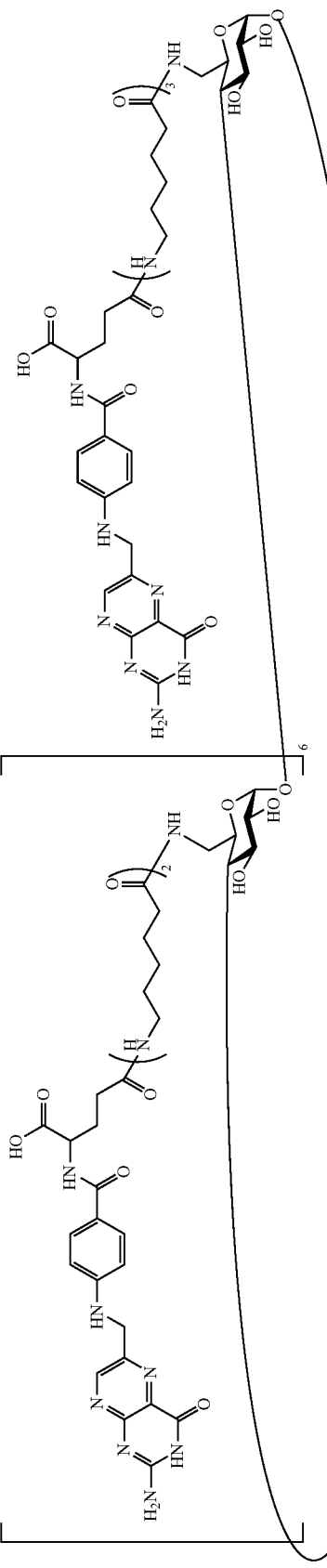
Exemplary compound 7
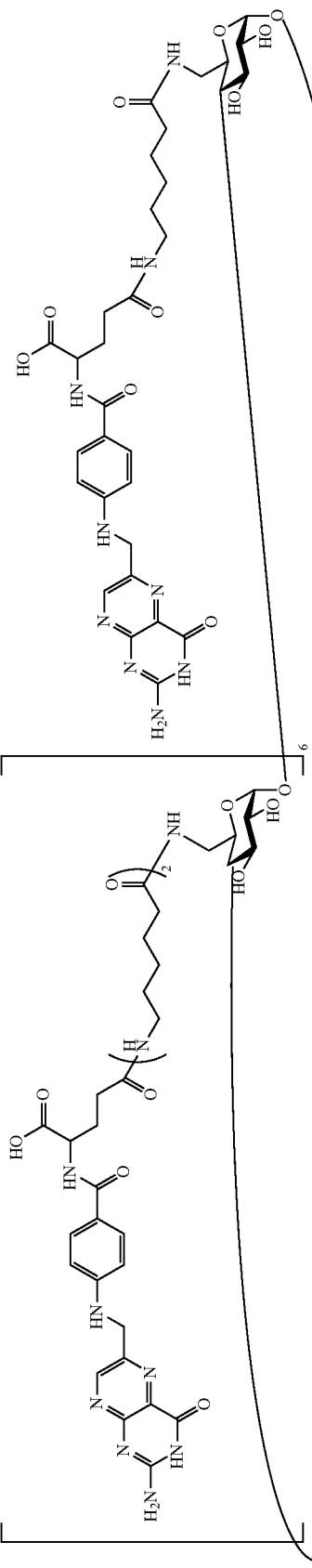
Exemplary compound 8

-continued
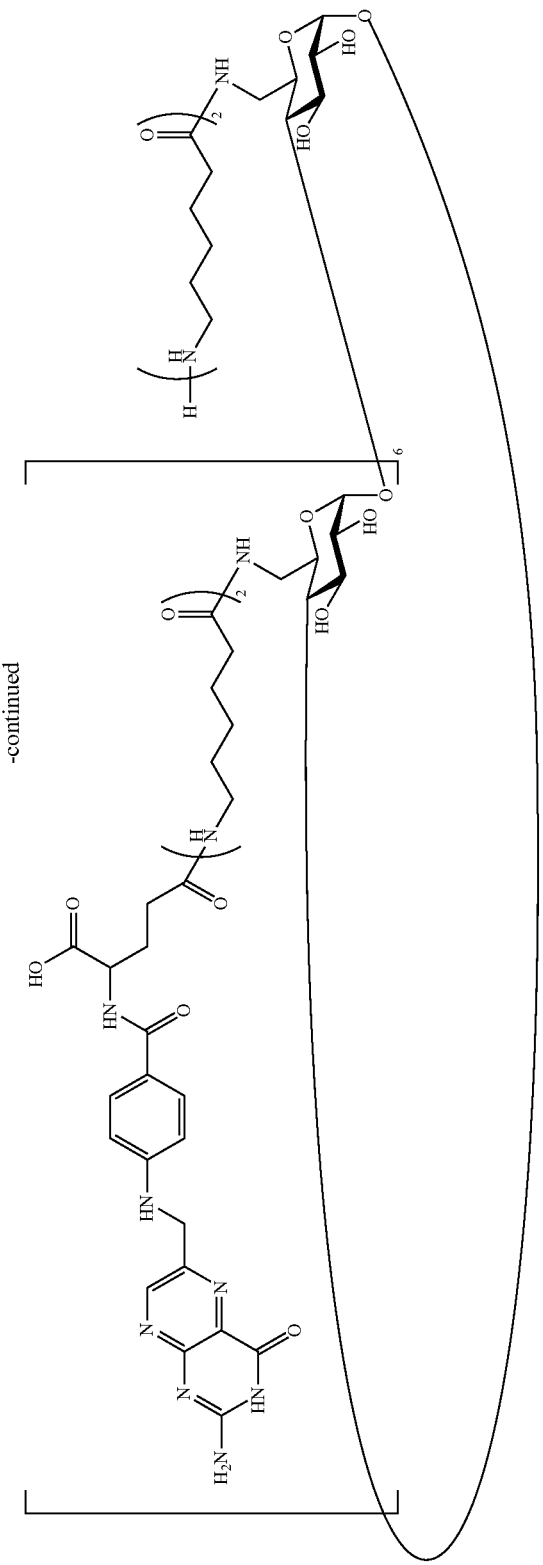
Exemplary compound 9
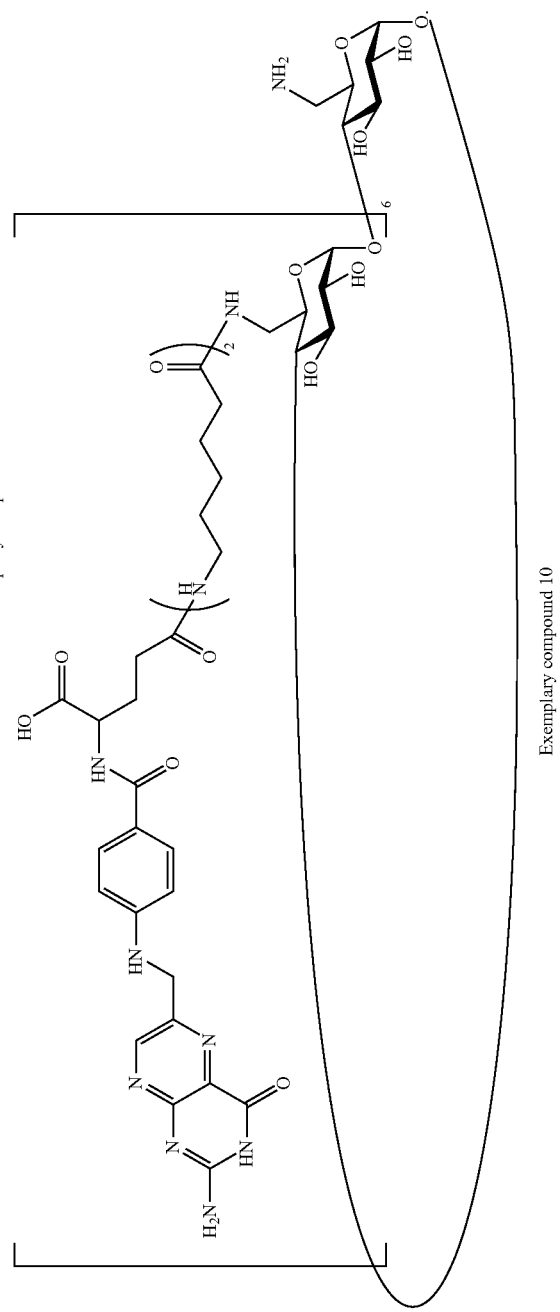
Exemplary compound 10

4. A process for producing a cyclodextrin compound modified with folic acid of any of claims 1-3, comprising the step of condensing folic acid with a cyclodextrin, the cyclodextrin having an amino group or an amino-oligocaproamide group substituted for a primary hydroxy group at position-6 in each glucopyranose constituting a cyclodextrin ring.

5. A targeting drug delivery agent containing the cyclodextrin compound of any one of claims 1-3.

6. A targeting pharmaceutical composition containing a drug and the cyclodextrin compound of any one of claims 1-3, wherein the drug is included in the cyclodextrin compound.

7. A targeting imaging agent containing an imaging agent and the cyclodextrin compound of any one of claims 1-3, wherein the imaging agent is included in the cyclodextrin compound.

* * * * *